(12) United States Patent
Hao et al.

(10) Patent No.: US 11,989,804 B2
(45) Date of Patent: May 21, 2024

(54) SYSTEMS AND METHODS FOR MEDICAL IMAGING

(71) Applicant: SHANGHAI UNITED IMAGING HEALTHCARE CO., LTD., Shanghai (CN)

(72) Inventors: Xin Hao, Shanghai (CN); Xiang Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 20 days.

(21) Appl. No.: 17/449,450

(22) Filed: Sep. 29, 2021

(65) Prior Publication Data

US 2022/0020186 A1    Jan. 20, 2022

Related U.S. Application Data

(62) Division of application No. 16/181,403, filed on Nov. 6, 2018, now Pat. No. 11,138,770.

(30) Foreign Application Priority Data

Nov. 6, 2017  (CN) .......................... 201711087639.8
Dec. 28, 2017 (CN) .......................... 201711459837.2

(51) Int. Cl.
*G06T 11/00*    (2006.01)
*A61B 5/00*     (2006.01)
(Continued)

(52) U.S. Cl.
CPC .......... *G06T 11/008* (2013.01); *A61B 5/0044* (2013.01); *A61B 5/346* (2021.01);
(Continued)

(58) Field of Classification Search
None
See application file for complete search history.

(56) References Cited

U.S. PATENT DOCUMENTS 5,984,954 A * 11/1999 Cohen .................... A61B 5/352
600/521
2004/0120450 A1    6/2004 Flohr et al.
(Continued)

FOREIGN PATENT DOCUMENTS

CN      103006209 A    4/2013
CN      103083036 A    5/2013
(Continued)

OTHER PUBLICATIONS

First Office Action in Chinese Application No. 201711087639.8 dated Feb. 3, 2020, 19 pages.
(Continued)

*Primary Examiner* — Leon Viet Q Nguyen
(74) *Attorney, Agent, or Firm* — METIS IP LLC

(57) ABSTRACT

The present disclosure relates to a method for analyzing an R-wave of an electrocardiogram (ECG) signal. The method includes obtaining an original ECG signal of a subject; filtering the original ECG signal; determining whether to trigger a search gate based on the filtered ECG signal, wherein the search gate is an instruction for detecting an R-wave on the original ECG signal; and detecting the R-wave on the original ECG signal in response to a determination of triggering the search gate.

18 Claims, 14 Drawing Sheets

(51) Int. Cl.
*A61B 5/346* (2021.01)
*A61B 5/352* (2021.01)
*A61B 6/00* (2006.01)
*A61B 6/03* (2006.01)
*A61B 6/50* (2024.01)
*G06T 7/00* (2017.01)
*A61B 5/0245* (2006.01)

(52) U.S. Cl.
CPC ............ *A61B 5/352* (2021.01); *A61B 5/7207* (2013.01); *A61B 5/7267* (2013.01); *A61B 5/7285* (2013.01); *A61B 6/032* (2013.01); *A61B 6/503* (2013.01); *A61B 6/504* (2013.01); *A61B 6/5205* (2013.01); *A61B 6/5264* (2013.01); *A61B 6/5288* (2013.01); *G06T 7/0012* (2013.01); *A61B 5/0245* (2013.01); *G06T 11/006* (2013.01); *G06T 2207/10081* (2013.01); *G06T 2207/10088* (2013.01); *G06T 2207/10104* (2013.01); *G06T 2207/20081* (2013.01); *G06T 2207/30048* (2013.01); *G06T 2207/30168* (2013.01); *G06T 2210/41* (2013.01); *G06T 2211/424* (2013.01)

(56) References Cited

U.S. PATENT DOCUMENTS

| | | | |
|---|---|---|---|
| 2006/0178591 A1* | 8/2006 | Hempfling | A61B 5/0816 600/509 |
| 2007/0167707 A1 | 7/2007 | Mistretta et al. | |
| 2008/0267342 A1 | 10/2008 | Grass et al. | |
| 2011/0033097 A1 | 2/2011 | Bruder et al. | |
| 2011/0251504 A1* | 10/2011 | Tereshchenko | A61B 5/341 600/512 |
| 2011/0319777 A1 | 12/2011 | Mehrotra et al. | |
| 2013/0237874 A1 | 9/2013 | Zoicas | |
| 2014/0277241 A1 | 9/2014 | Bleich et al. | |
| 2014/0334708 A1* | 11/2014 | Sakata | A61B 6/5288 382/131 |
| 2015/0164340 A1* | 6/2015 | Bedingham | A61B 5/282 600/513 |
| 2015/0342489 A1 | 12/2015 | Bhaumik et al. | |
| 2016/0035112 A1 | 2/2016 | Lou et al. | |
| 2017/0086752 A1* | 3/2017 | Baxi | A61B 5/316 |
| 2017/0242974 A1* | 8/2017 | Zhao | A61B 5/0245 |
| 2017/0319088 A1* | 11/2017 | George | A61B 5/726 |
| 2018/0242942 A1 | 8/2018 | Jackson et al. | |
| 2019/0030352 A1* | 1/2019 | Sullivan | A61N 1/3987 |

FOREIGN PATENT DOCUMENTS

| | | |
|---|---|---|
| CN | 103549950 A | 2/2014 |
| CN | 103584854 A | 2/2014 |
| CN | 103705234 A | 4/2014 |
| CN | 104000581 A | 8/2014 |
| CN | 104161510 A | 11/2014 |
| CN | 104586384 A | 5/2015 |
| CN | 105030228 A | 11/2015 |
| CN | 105125199 A | 12/2015 |
| CN | 105125207 A | 12/2015 |
| CN | 105232027 A | 1/2016 |
| CN | 106529425 A | 3/2017 |
| CN | 107041743 A | 8/2017 |
| CN | 107095665 A | 8/2017 |
| CN | 107184200 A | 9/2017 |
| CN | 107239684 A | 10/2017 |
| KR | 20120131043 A | 12/2012 |
| KR | 20130085168 A | 7/2013 |

OTHER PUBLICATIONS

The Second Office Action in Chinese Application No. 201711087639.8 dated Oct. 21, 2020, 22 pages.

Wang, Qi et al., Diagnosis of Obstructive Coronary Artery Disease Using CT Coronary Angiography Combined with CT First-pass Myocardial Perfusion Imaging at Rest, J South Med Univ, 33(6): 819-825, 2013.

Zeng, Xianqiang et al., Study of CT Tomograph and Reconstruction and DSA Before Stent Placement in the Aortic Cavity, Journal of Medical Forum, 29(19): 110-111, 2008.

Béatrice Perrenot et al., Motion Correction for Coronary Stent Reconstruction From Rotational X-ray Projection Sequences, IEEE Transactions on Medical Imaging, 26(10): 1412-1423, 2007.

* cited by examiner

SYSTEMS AND METHODS FOR MEDICAL IMAGING

CROSS-REFERENCE TO RELATED APPLICATIONS

This application is a divisional application of U.S. application Ser. No. 16/181,403 filed on Nov. 6, 2018, which claims priority to Chinese Patent Application No. 201711087639.8 filed on Nov. 6, 2017, and Chinese Patent Application No. 201711459837.2 filed on Dec. 28, 2017, the contents of which are incorporated herein by reference.

TECHNICAL FIELD

The present disclosure generally relates to medical imaging, and more particularly, systems and methods for reconstructing a cardiac image using an imaging device.

BACKGROUND

A medical imaging device, such as a computed tomography (CT), a magnetic resonance imaging (MRI), a positron emission computed tomography (PET), is widely used in a field of disease diagnosis. For example, the CT may scan a heart of a subject, and generate scan data. The CT may reconstruct a cardiac image of the subject based on the scan data. In some occasions, due to a motion blur caused by heart beats, there may be a pulsatile artifact in the reconstructed cardiac image. The cardiac image with the pulsatile artifact may not provide accurate information for the disease diagnosis. It is desired to develop systems and methods to provide high quality medical image in medical imaging to benefit disease diagnosis.

SUMMARY

According to a first aspect of the present disclosure, a method for reconstructing a medical image by using an imaging device may include one or more operations. The one or more operations may be implemented on a computing device having one or more processors and one or more storage devices. The one or more processors may obtain scan data that is captured by scanning a heart of a subject with the imaging device. The one or more processors may obtain electrocardiogram (ECG) data that is captured during the scans of the heart of the subject, the ECG data corresponding to a plurality of cardiac cycles. The one or more processors may determine first scan data from the scan data, the first scan data corresponding to a first time period of each of the plurality of cardiac cycles. The one or more processors may reconstruct the cardiac image based on the first scan data. For obtaining the reconstructed cardiac image that satisfies a requirement of diagnose, the one or more processors may perform one or more iterations for the reconstructed cardiac image. For each of the one or more iterations, the one or more processors may determine whether there is a pulsatile artifact in the reconstructed cardiac image. The one or more processors may determine a second time period of at least one cardiac cycle based on the pulsatile artifact. The one or more processors may reconstruct the cardiac image based on the scan data and the second time period. The one or more processors may complete the one or more iterations until there is no pulsatile artifact substantially the reconstructed cardiac image.

In some embodiments, the one or more processors may determine second scan data associated with the pulsatile artifact, the second scan data being at least one portion of the first scan data. The one or more processors may determine the at least one cardiac cycle corresponding to the second scan data based on the ECG data and a capture time of the second scan data. The one or more processors may determine the second time period of the at least one cardiac cycle.

In some embodiments, the one or more processors may determine a first image sequence based on the first scan data. The one or more processors may further reconstruct the cardiac image based on the first image sequence.

In some embodiments, the one or more processors may determine at least one first image with the pulsatile artifact from the first image sequence. The one or more processors may determine the second time period of the at least one cardiac cycle corresponding to the at least one first image with the pulsatile artifact.

In some embodiments, the one or more processors may determine third scan data based on the scan data, the at least one cardiac cycle corresponding to the at least one first image with the pulsatile artifact, and the second time period. The one or more processors may reconstruct at least one second image, corresponding to the at least one cardiac cycle corresponding to the at least one first image with the pulsatile artifact, based on the third scan data. The one or more processors may determine a second image sequence based on the first image sequence and the at least one second image. The one or more processors may reconstruct the cardiac image based on the second image sequence.

In some embodiments, the one or more processors may determine whether there is a pulsatile artifact in the reconstructed cardiac image based on a first machine-learned identification model. The first machine-learned identification model may be trained based on a plurality of cardiac images with the pulsatile artifact.

According to another aspect of the present disclosure, a system for reconstructing a medical image by using an imaging device may include at least one storage device including a set of instructions, and at least one processor in communication with the at least one storage device. When executing the set of instructions, the at least one processor may obtain scan data that is captured by scanning a heart of a subject with the imaging device. The at least one processor may obtain electrocardiogram (ECG) data that is captured during the scans of the heart of the subject, the ECG data corresponding to a plurality of cardiac cycles. The at least one processor may determine first scan data from the scan data, the first scan data corresponding to a first time period of each of the plurality of cardiac cycles. The at least one processor may reconstruct the cardiac image based on the first scan data. The at least one processor may perform one or more iterations for the reconstructed cardiac image. For each of the one or more iterations, the at least one processor may determine whether there is a pulsatile artifact in the reconstructed cardiac image. The at least one processor may determine a second time period of at least one cardiac cycle based on the pulsatile artifact. The at least one processor may reconstruct the cardiac image based on the scan data and the second time period. The at least one processor may complete the one or more iterations until there is no pulsatile artifact substantially the reconstructed cardiac image.

According to yet another aspect of the present disclosure, a non-transitory computer readable medium may comprise at least one set of instructions for reconstructing a medical image. The at least one set of instructions may be executed by one or more processors of a computer device. The one or more processors may obtain scan data that is captured by scanning a heart of a subject with the imaging device. The one or more processors may obtain electrocardiogram (ECG) data that is captured during the scans of the heart of the subject, the ECG data corresponding to a plurality of cardiac cycles. The one or more processors may determine first scan data from the scan data, the first scan data corresponding to a first time period of each of the plurality of cardiac cycles. The one or more processors may reconstruct the cardiac image based on the first scan data. The one or more processors may perform one or more iterations for the reconstructed cardiac image. For each of the one or more iterations, the one or more processors may determine whether there is a pulsatile artifact in the reconstructed cardiac image. The one or more processors may determine a second time period of at least one cardiac cycle based on the pulsatile artifact. The one or more processors may reconstruct the cardiac image based on the scan data and the second time period. The one or more processors may complete the one or more iterations until there is no pulsatile artifact substantially the reconstructed cardiac image.

According to yet another aspect of the present disclosure, a method for analyzing an R-wave of an electrocardiogram (ECG) signal may include one or more operations. The one or more operations may be implemented on a computing device having one or more processors and one or more storage devices. The one or more processors may obtain an original ECG signal of a subject. The one or more processors may filter the original ECG signal. The one or more processors may determine whether to trigger a search gate based on the filtered ECG signal, wherein the search gate is an instruction for detecting an R-wave on the original ECG signal. The one or more processors may detect the R-wave on the original ECG signal in response to a determination of triggering the search gate.

In some embodiments, the one or more processors may filter the original ECG signal based on an infinite impulse response (IIR) low pass filter.

In some embodiments, the one or more processors may determine a differential signal based on the filtered ECG signal. The one or more processors may determine to trigger the search gate if the differential signal is equal to or greater than a gate threshold.

In some embodiments, the one or more processors may determine a differential signal based on the filtered ECG signal. The one or more processors may determine an amplified signal based on the differential signal. The one or more processors may determine to trigger the search gate if the amplified signal is equal to or greater than the gate threshold.

In some embodiments, the gate threshold may be determined based on values of N samples of the filtered ECG signal. The N samples may include a current sample and N−1 previous samples, and N is an integer and equal to or greater than 1.

In some embodiments, for each of a plurality of samples of the original ECG signal, the one or more processors may determine a difference between the sample and a signal baseline. The one or more processors may determine whether the difference is equal to or greater than an amplitude threshold. In response to a determination that the difference is equal to or greater than the amplitude threshold, the one or more processors may determine a position of the sample that has a maximum value among absolute values of a plurality of the differences, as the position of the R-wave.

In some embodiments, the signal baseline may associate with values of M samples of the original ECG signal. The M samples may include the current sample and M−1 previous samples, and M is an integer and equal to or greater than 1.

In some embodiments, the amplitude threshold may associate with the plurality of differences between the plurality of samples and the signal baseline.

According to another aspect of the present disclosure, a system for analyzing an R-wave of an electrocardiogram (ECG) signal may include at least one storage device including a set of instructions, and at least one processor in communication with the at least one storage device. When executing the set of instructions, the at least one processor may obtain an original ECG signal of a subject. The at least one processor may filter the original ECG signal. The at least one processor may determine whether to trigger a search gate based on the filtered ECG signal, wherein the search gate is an instruction for detecting an R-wave on the original ECG signal. The at least one processor may detect the R-wave on the original ECG signal in response to a determination of triggering the search gate.

According to yet another aspect of the present disclosure, a non-transitory computer readable medium may comprise at least one set of instructions for analyzing an R-wave of an electrocardiogram (ECG) signal. The at least one set of instructions may be executed by one or more processors of a computer device. The one or more processors may obtain an original ECG signal of a subject. The one or more processors may filter the original ECG signal. The one or more processors may determine whether to trigger a search gate based on the filtered ECG signal, wherein the search gate is an instruction for detecting an R-wave on the original ECG signal. The one or more processors may detect the R-wave on the original ECG signal in response to a determination of triggering the search gate.

According to yet another aspect of the present disclosure, a method for reconstructing a medical image by using an imaging device may include one or more operations. The one or more operations may be implemented on a computing device having one or more processors and one or more storage devices. The one or more processors may obtain an ECG signal of a heart of a subject. The one or more processors may detect an R-wave of a cardiac cycle of the ECG signal. In response to the detection of the R-wave, the one or more processors may operate the imaging device to perform scans of the heart to generate scan data, wherein a starting time of each of the scans is determined based on the R-wave of each cardiac cycle of the ECG signal. The one or more processors may obtain ECG data that is captured during the scans of the heart, the ECG data corresponding to a plurality of cardiac cycles of the ECG signal. The one or more processors may determine first scan data from the scan data, the first scan data corresponding to a first time period of each of the plurality of cardiac cycles. The one or more processors may reconstruct the cardiac image based on the first scan data. The one or more processors may perform one or more iterations for the reconstructed cardiac image. For each of the one or more iterations, the one or more processors may determine whether there is a pulsatile artifact in the reconstructed cardiac image. The one or more processors may determine a second time period of at least one cardiac cycle based on the pulsatile artifact. The one or more processors may reconstruct the cardiac image based on the scan data and the second time period. The one or more processors may complete the one or more iterations until there is no pulsatile artifact substantially the reconstructed cardiac image.

According to yet another aspect of the present disclosure, a system for reconstructing a medical image by using an imaging device may include at least one storage device including a set of instructions, and at least one processor in communication with the at least one storage device. The at least one processor may obtain an ECG signal of a heart of a subject. The at least one processor may detect an R-wave of a cardiac cycle of the ECG signal. In response to the detection of the R-wave, the at least one processor may operate the imaging device to perform scans of the heart to generate scan data, wherein a starting time of each of the scans is determined based on the R-wave of each cardiac cycle of the ECG signal. The at least one processor may obtain ECG data that is captured during the scans of the heart, the ECG data corresponding to a plurality of cardiac cycles of the ECG signal. The at least one processor may determine first scan data from the scan data, the first scan data corresponding to a first time period of each of the plurality of cardiac cycles. The at least one processor may reconstruct the cardiac image based on the first scan data. The at least one processor may perform one or more iterations for the reconstructed cardiac image. For each of the one or more iterations, the at least one processor may determine whether there is a pulsatile artifact in the reconstructed cardiac image. The at least one processor may determine a second time period of at least one cardiac cycle based on the pulsatile artifact. The at least one processor may reconstruct the cardiac image based on the scan data and the second time period. The at least one processor may complete the one or more iterations until there is no pulsatile artifact substantially the reconstructed cardiac image.

According to yet another aspect of the present disclosure, a non-transitory computer readable medium may comprise at least one set of instructions for reconstructing a medical image by using an imaging device. The at least one set of instructions may be executed by one or more processors of a computer device. The at least one processor may obtain an ECG signal of a heart of a subject. The at least one processor may detect an R-wave of a cardiac cycle of the ECG signal. In response to the detection of the R-wave, the at least one processor may operate the imaging device to perform scans of the heart to generate scan data, wherein a starting time of each of the scans is determined based on the R-wave of each cardiac cycle of the ECG signal. The at least one processor may obtain ECG data that is captured during the scans of the heart, the ECG data corresponding to a plurality of cardiac cycles of the ECG signal. The at least one processor may determine first scan data from the scan data, the first scan data corresponding to a first time period of each of the plurality of cardiac cycles. The at least one processor may reconstruct the cardiac image based on the first scan data. The at least one processor may perform one or more iterations for the reconstructed cardiac image. For each of the one or more iterations, the at least one processor may determine whether there is a pulsatile artifact in the reconstructed cardiac image. The at least one processor may determine a second time period of at least one cardiac cycle based on the pulsatile artifact. The at least one processor may reconstruct the cardiac image based on the scan data and the second time period. The at least one processor may complete the one or more iterations until there is no pulsatile artifact substantially the reconstructed cardiac image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
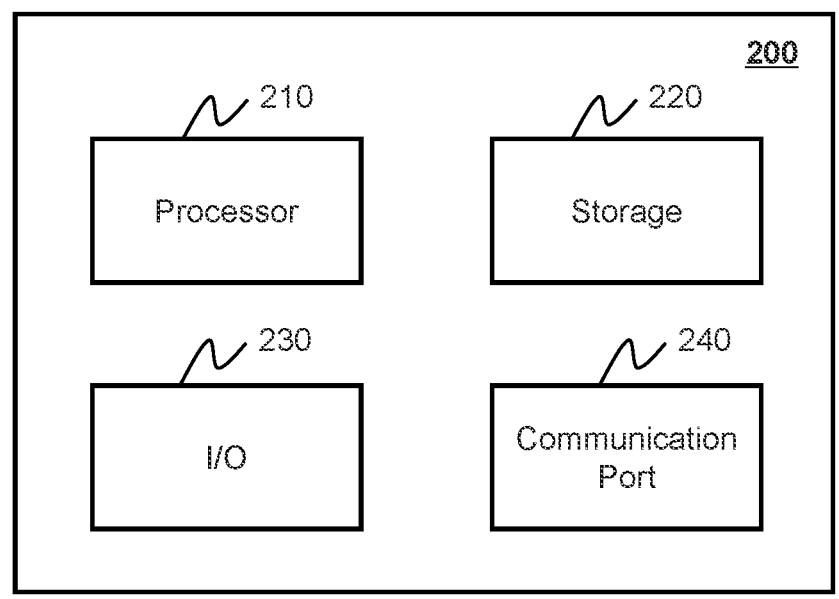
FIG. 2 is a block diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

The various embodiments of the present disclosure may be provided as an imaging system configured to reconstruct a medical image (e.g., a cardiac image). In some embodiments, the system may detect an R-wave based on the ECG data. The system may perform scans of a subject based on the detected R-wave. The system may reconstruct the cardiac image based on scan data and ECG data. If there is a pulsatile artifact in the reconstructed cardiac image, the system may perform one or more iterations for reconstructing a cardiac image to remove or eliminate the pulsatile artifact based on the scan data and the ECG data.

Figure 1:
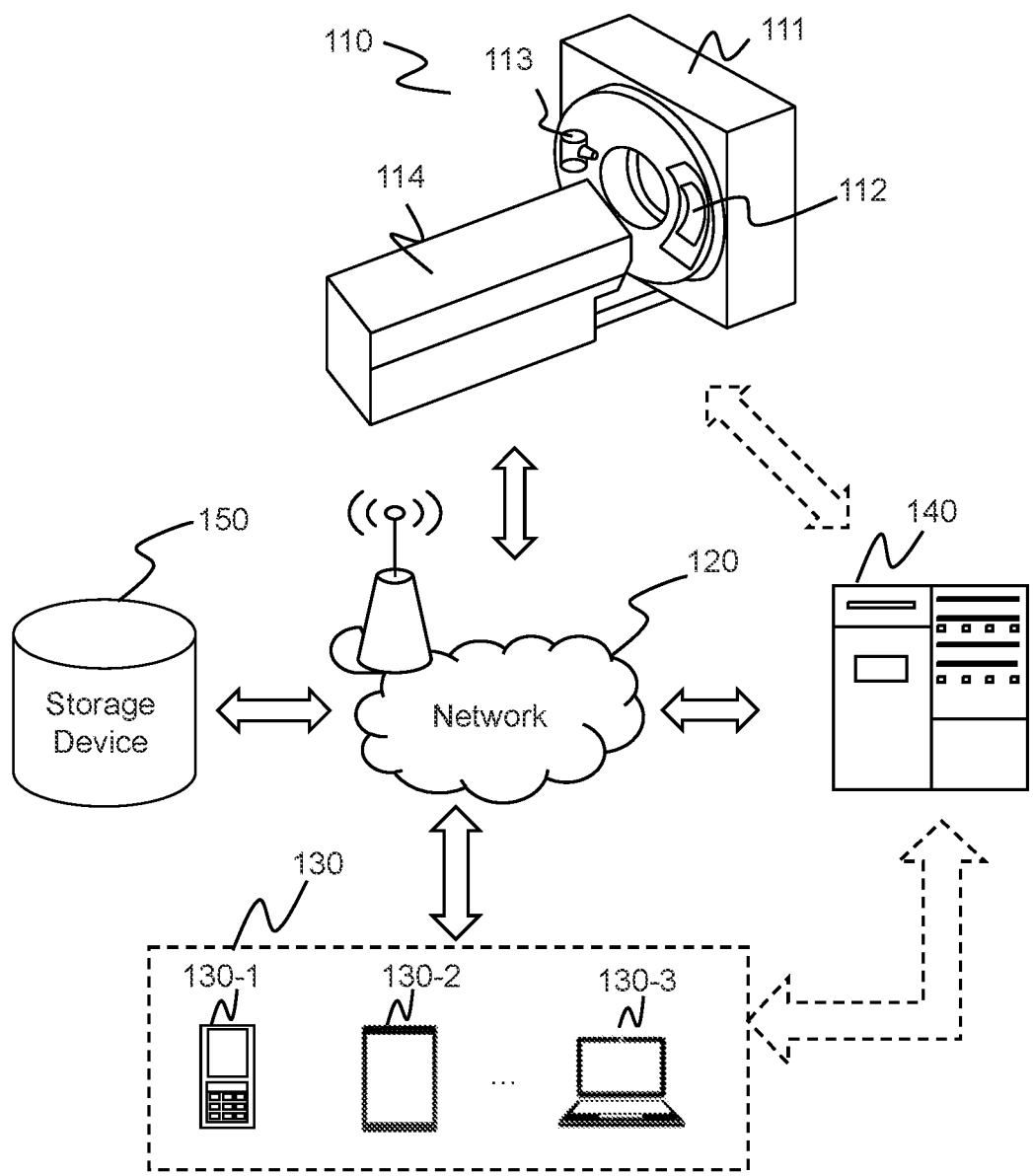
FIG. 1 is a schematic diagram illustrating an exemplary imaging system according to some embodiments of the present disclosure.

FIG. 1 is a schematic diagram illustrating an exemplary imaging system according to some embodiments of the present disclosure. As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the imaging device 110 may include a computed tomography (CT) scanner, a positron emission tomography (PET) scanner, a magnetic resonance imaging (MRI) scanner, a multi-modality scanner, or the like, or a combination thereof. Exemplary CT scanner may include a Multi-detector computed tomography (MDCT), a Multi-slice computed tomography (MSCT), or the like, or any combination thereof. Exemplary multi-modality scanners may include a computed tomography-positron emission tomography (CT-PET) scanner, a computed tomography-magnetic resonance imaging (CT-MRI) scanner, or the like, or any combination thereof.

In some embodiments, the imaging device 110 may include a gantry 111, a detector 112, an X-ray generator 113, and a scanning table 114. The detector 112 and the X-ray generator 113 may be oppositely mounted on the gantry 111. A scan object may be placed on the scanning table 114 and moved into a detection tunnel (e.g., a space between the detector 112 and the X-ray generator 113) of the imaging device 110. The scan object may be biological or non-biological. Merely by way of example, the scan object may include a patient, a man-made object, etc. As another example, the scan object may include a specific portion, organ, and/or tissue of the patient. For example, the scan object may include head, brain, neck, body, shoulder, arm, thorax, cardiac, stomach, blood vessel, soft tissue, knee, feet, or the like, or any combination thereof. In the present disclosure, "subject", "object" or "scan object" are used interchangeably.

The X-ray generator 113 may emit radiation rays to scan the scan object that is placed on the scanning table 114. The radiation rays may include X-rays, γ-rays, α-rays, ultraviolet, laser, neutron, proton, or the like, or a combination thereof. The detector 112 may receive the radiation rays passed through the scan object. In some embodiments, the detector 112 may include a plurality of detector units, which may be arranged in a channel direction and a row direction. The detector 112 may include a scintillation detector (e.g., a cesium iodide detector) or a gas detector.

The network 120 may facilitate exchange of information and/or data. In some embodiments, one or more components of the imaging system 100 (e.g., the imaging device 110, the terminal 130, the processing device 140, or the storage device 150) may send information and/or data to another component(s) in the imaging system 100 via the network 120. For example, the processing device 140 may obtain, via the network 120, an image from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the imaging device 110. In some embodiments, the terminal 130 may operate the imaging device 110 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the imaging device 110, the terminal 130, or the storage device 150. For example, the processing device 140 may reconstruct a cardiac image based on the scan data and/or the ECG data. As another example, the processing device 140 may analyze the ECG data, and detect an R-wave based on the ECG data. As a further example, the processing device 140 may receive an instruction for operating the imaging device 110 to perform scans of a subject. The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the processing device 140. In some embodiments, the storage device 150 may store data and/or instructions that the processing device 140 may execute or use to perform exemplary methods described in the present disclosure. For example, the storage device 150 may store data and/or instructions that the processing device 140 may execute or use to reconstruct a medical image. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

FIG. 2 is a schematic diagram illustrating hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 140 and/or the terminal 130 may be implemented on the computing device 200.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal 130, the storage device 150, and/or any other component of the imaging system 100. For example, the processor 210 may obtain scan data and/or ECG data from the storage device 150, detect an R-wave based on the ECG data, and reconstruct a cardiac image based on the scan data and the ECG data. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal 130, the storage device 150, or any other component of the imaging system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instructions) for the processing device 140 to analyze an ECG signal, and detect the R-wave based on the ECG signal. As another example, the storage 220 may store a program (e.g., in the form of computer-executable instructions) for the processing device 140 to reconstruct a cardiac image that is without a pulsatile artifact substantially.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
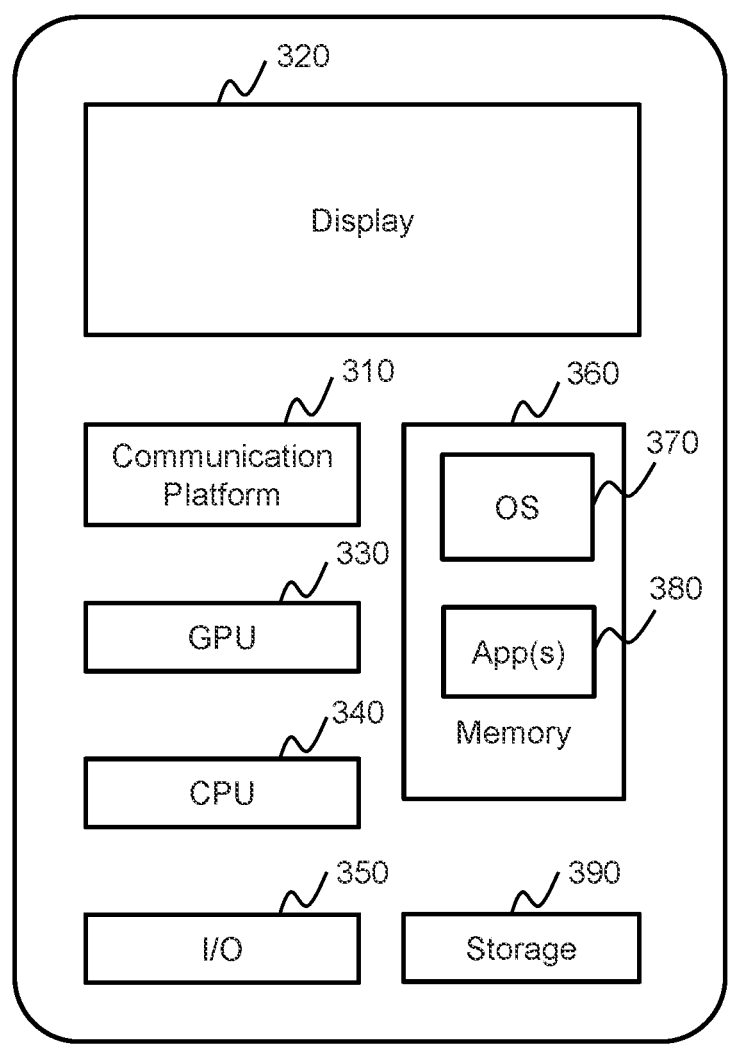
FIG. 3 is a schematic diagram illustrating hardware and/or software components of an exemplary mobile device according to some embodiments of the present disclosure.

FIG. 3 is a schematic diagram illustrating hardware and/or software components of a mobile device according to some embodiments of the present disclosure. In some embodiments, the processing device 140 and/or the terminal 130 may be implemented on the mobile device 300. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate high-quality image of a scan object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
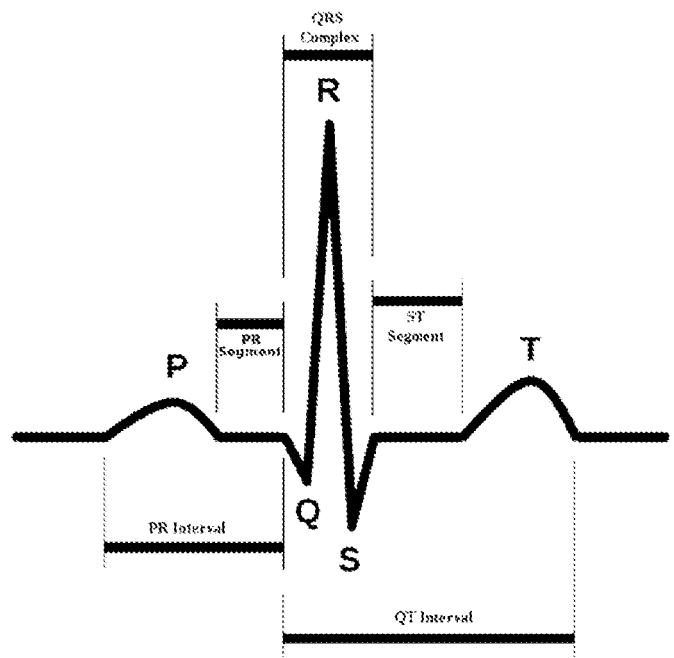
FIGS. 4A and 4B are schematic diagrams illustrating exemplary electrocardiogram (ECG) according to some embodiments of the present disclosure.
Figure 4B:
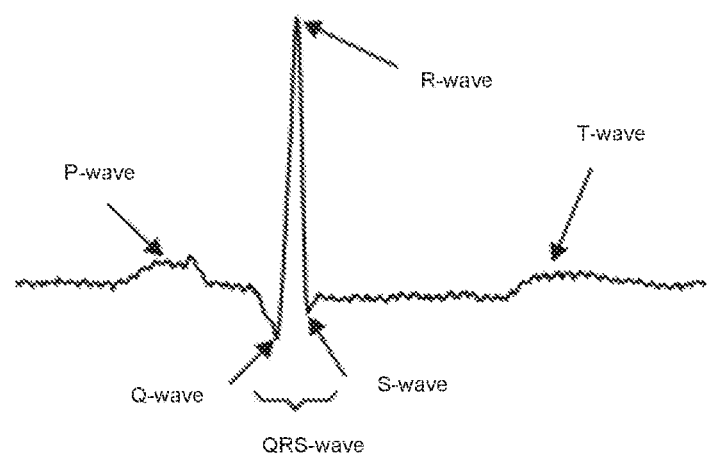

FIG. 4A is a schematic diagram illustrating exemplary ECG indicating normal sinus rhythm for a human heart. The ECG may include a plurality of cycles indicating normal sinus rhythm. Generally, each cycle may include a P-wave, a QRS complex, a T-wave, as shown in FIG. 4A. The QRS complex may include a Q-wave, an R-wave and an S-wave. As shown in FIG. 4A, for each cycle of the ECG, a PR interval refers to a duration that extends from the beginning of the P-wave to the beginning of the QRS complex. A PR segment refers to a duration that extends from the end of the P-wave to the beginning of the QRS complex. A QT interval refers to a duration that extends from the beginning of the QRS complex to the end of the T-wave. An ST segment refers to a duration that extends from the end of the QRS complex to the beginning of the T-wave. FIG. 4B is similar to FIG. 4A, which represents an exemplary normal ECG including a P-wave, a QRS complex, and a T-wave. Seen from FIG. 4A and FIG. 4B, for the ECG, the R-wave of the QRS complex may be the most significant wave among the components of one cycle of the ECG (e.g., the P-wave, the QRS complex, the T-wave). In some embodiments, the peak may appear as an upward peak or a downward peak. As shown in FIG. 4A or FIG. 4B, the R-wave appears as the upward peak. In some embodiments, the ECG may be analyzed by dividing one or more cardiac cycles. For example, the R-wave may be designated as a beginning and/or an end of the cardiac cycle, which records the performance of the human heart from the beginning of one heartbeat to the end of the one heartbeat (or the beginning of a next heartbeat). The cardiac cycle may refer to a duration between two adjacent R-waves. As used herein, one cardiac cycle may be denoted as an R-R interval, or an R-R for short. An entire ECG of the subject may include a plurality of cardiac cycles.

Figure 5:
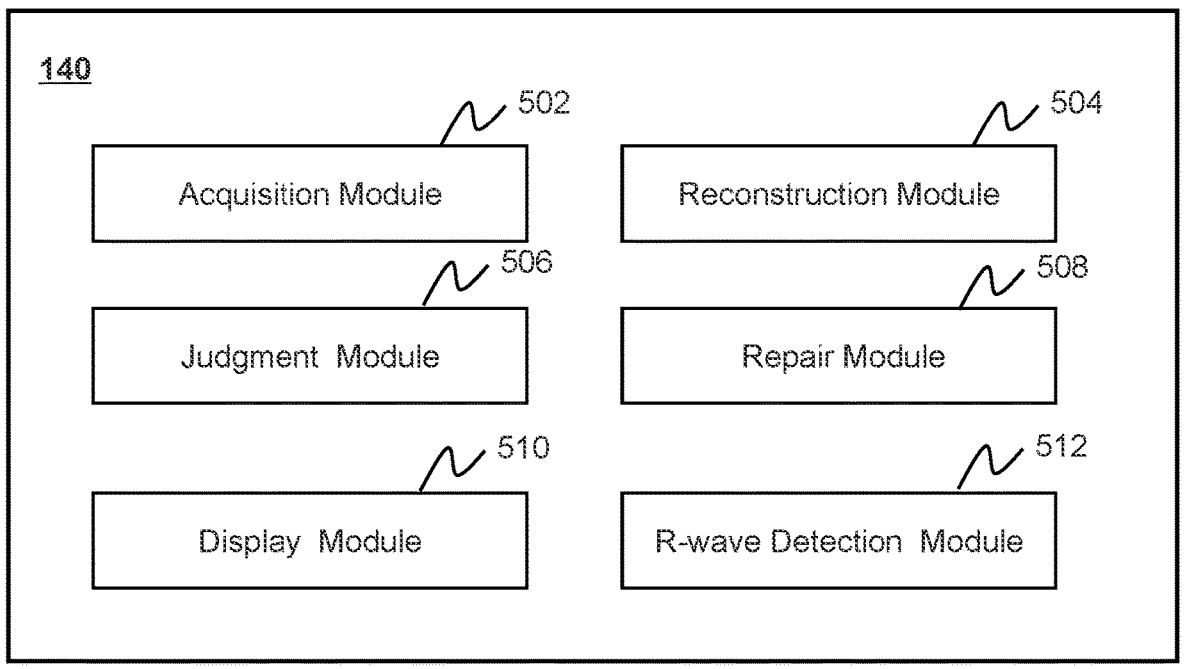
FIG. 5 is a block diagram illustrating an exemplary processing device according to some embodiments of the present disclosure.

FIG. 5 is a schematic diagram illustrating an exemplary processing device according to some embodiments of the present disclosure. As illustrated in FIG. 5, the processing device 140 may include an acquisition module 502, a reconstruction module 504, a judgment module 506, a repair module 508, a display module 510, and an R-wave detection module 512. At least a portion of the processing device 140 may be implemented on the computing device 200 as illustrated in FIG. 2 or the mobile device 300 as illustrated in FIG. 3.

The acquisition module 502 may obtain scan data that is captured by scanning a heart of a subject (e.g., a patient) with the imaging device (e.g., the imaging device 110). The imaging device 110 may scan the heart of the subject to generate the scan data. In some embodiments, the scan data may be stored in a storage medium (e.g., the storage device 150, and/or the storage 220). The acquisition module 502 may obtain the scan data from the storage medium. In some embodiments, the acquisition module 502 may directly obtain the scan data in real time from the imaging device 110 during the scans.

The acquisition module 502 may obtain ECG data that is captured during the scans of the heart of the subject. The ECG data may include an ECG signal corresponding to a plurality of cardiac cycles. In some embodiments, the ECG data may be detected by a generic ECG acquisition collector integrated in the imaging device 110 or separated from the imaging device 110. The acquisition module 502 may obtain the ECG data from the generic ECG acquisition collector directly. In some embodiments, the ECG data may be stored in a storage medium (e.g., the storage device 150, and/or the storage 220) of the imaging system 100. The acquisition module 502 may obtain the ECG data from the storage medium. In some embodiments, during the scans, the acquisition module 502 may obtain the ECG data and/or the scan data synchronously in real time or substantially real time.

The reconstruction module 504 may reconstruct a medical image (e.g., a cardiac image) based on the scan data and/or the ECG data. In some embodiments, the reconstruction module 504 may determine first scan data from the scan data. The first scan data may include scan data corresponding to a first time period of each of the plurality of cardiac cycles. The first time period refers to a certain phase of each of the plurality of cardiac cycles. The first time period may be given as percentage of a duration of the cardiac cycle. The duration of the cardiac cycle may be the time interval between two adjacent R-waves, that is, an R-R interval (i.e., an R-R for short). For example, the first time period may predetermined as 10% R-R, 20% R-R, 30% R-R, 40% R-R, 50% R-R, 60% R-R, 70% R-R, 80% R-R, and so on. In some embodiments, the reconstruction module 504 may determine a first reconstruction phase based on the first time period and an imaging window. The imaging window may indicate a width of the first reconstruction phase, for example, the width is equal to 10% R-R. In some embodiments, the first reconstruction phase may be a sum of the first time period and the imaging window. In some embodiments, the scan data corresponding to the first reconstruction phase may be used to reconstruct an image (e.g., a slice image). The reconstruction module 504 may determine a plurality of first reconstruction phases for the plurality of cardiac cycles. The reconstruction module 504 may determine the first scan data that includes the scan data corresponding to the plurality of first reconstruction phases. The reconstruction module 504 may reconstruct the cardiac image based on the first scan data. The reconstructed cardiac image may include a first image sequence or a three-dimensional (3D) image.

In some embodiments, the reconstruction module 504 may reconstruct each first image of the first image sequence based on the scan data corresponding to the first reconstruction phase that is associated with the first scan data. Exemplary image reconstruction techniques may include filtered back projection (FBP), an algebraic reconstruction technology (ART), a statistical reconstruction (SR) algorithm, or the like, or any combination thereof.

In some embodiments, the reconstruction module 504 may reconstruct the 3D cardiac image based on the first image sequence by using a 3D reconstruction method. Exemplary 3D reconstruction method may include a surface rendering method, a volume rendering method, or the like, or any combination thereof. Exemplary surface rendering method may include the shortest diagonal method, a Cuberille method, a Dividing Cubes method, a Marching Cubes (MC) method, or the like, or any combination thereof. Exemplary volume rendering method may include a ray casting method, a splatting method, a shear-warp method, a 3D texture-mapping hardware, or the like, or any combination thereof.

The judgment module 506 may be configured to perform judgmental functions. For example, the judgment module 506 may determine whether there is a pulsatile artifact in the reconstructed cardiac image. In some embodiments, the judgment module 506 may use a first machine-learned identification model to determine whether there is the pulsatile artifact in the reconstructed 3D cardiac image. For example, the reconstructed 3D cardiac image may be as input of the first machine-learned identification model. If the output value is greater than or equal to a threshold, it is determined that there is the pulsatile artifact in the input cardiac image. If the output value is less than the threshold, it is determined that there is no pulsatile artifact in the input cardiac image. In some embodiments, the judgment module 506 may determine whether there is a pulsatile artifact in the reconstructed cardiac image based on whether one or more vessels or tissues in the reconstructed cardiac image are continuous. For example, if an experienced user judges that the one or more vessels or tissues in the reconstructed cardiac image are discontinuous, it is determined that there is the pulsatile artifact in the reconstructed cardiac image. In some embodiments, the judgment module 506 may determine whether there is a pulsatile artifact in the reconstructed cardiac image based on one or more image quality parameters. The one or more image quality parameters may include an image uniformity, a high contrast resolution, a low contrast resolution, a signal noise ratio (SNR), a CT number linearity, or the like, or any combination thereof. For example, if at least one image quality parameter is less than a predetermined quality threshold, the judgment module 506 may determine that there is the pulsatile artifact in the reconstructed cardiac image. For those skilled in the art, the pulsatile artifact may cause image degradation, and the degraded image may not satisfy a requirement of diagnose. The judgment module 506 may determine that the cardiac image with the pulsatile artifact is an unqualified image. Upon occurrence of the unqualified image, the repair module 508 may repair the unqualified image as qualified image. The term "qualified image" means that the image satisfy the requirement of diagnose. Specifically, the qualified image satisfies the one or more image quality parameters.

The repair module 508 may reconstruct a cardiac image that is without the pulsatile artifact substantially. In some embodiments, in response to a determination that there is the pulsatile artifact in the reconstructed cardiac image, the repair module 508 may determine at least one first image with the pulsatile artifact from the first image sequence. The repair module 508 may determine a second time period of the at least one cardiac cycle corresponding to the at least one first image with the pulsatile artifact. The second time period may be similar to the first time period, that is, a certain phase of each cardiac cycle (e.g., 80% R-R). The second time period may also be given as percentage of a duration of the cardiac cycle. The repair module 508 may adjust the first time period corresponding to the at least one cardiac cycle to the second time period. The second time period may be different than the first time period. The repair module 508 may determine third scan data based on the scan data, the at least one cardiac cycle corresponding to the at least one first image with the pulsatile artifact, and the second time period. For example, for each of the at least one cardiac cycle corresponding to the at least one first image with the pulsatile artifact, the repair module 508 may determine a second reconstruction phase based on the second time period and the imaging window. The second reconstruction phase may be a sum of the second time period and the imaging window. The repair module 508 may determine sub-third scan data that includes scan data corresponding to the second reconstruction phase. The repair module 508 may determine the third scan data that includes each sub-third scan data corresponding to the second reconstruction phase of each of the at least one cardiac cycle.

In some embodiments, the repair module 508 may further reconstruct at least one second image, corresponding to the at least one cardiac cycle corresponding to the at least one first image with the pulsatile artifact, based on the third scan data. In some embodiments, the repair module 508 may determine a second image sequence based on the first image sequence and the at least one second image, and reconstruct the 3D cardiac image based on the second image sequence. More descriptions of reconstructing the cardiac image that is without the pulsatile artifact may be found elsewhere in the present disclosure (e.g., FIG. 7, FIGS. 8A-8B, and the descriptions thereof).

The display module 510 may display scan data, ECG data, and/or the reconstructed image. In some embodiments, the display module 510 may display information associated with the reconstruction in various forms, such as messages, images, videos, and so on.

The R-wave detection module 512 may be configured to analyze an R-wave, in particular, to detect the R-wave of each cardiac cycle based on the ECG data.

The R-wave detection module 512 may obtain an original ECG signal of a subject. In some embodiments, the obtained original ECG signal may be a digital ECG signal. The original ECG signal may include a plurality of samples. During the scans, the ECG acquisition collector may collect a sample in a pre-determined sampling rate in real time.

Figure 6:
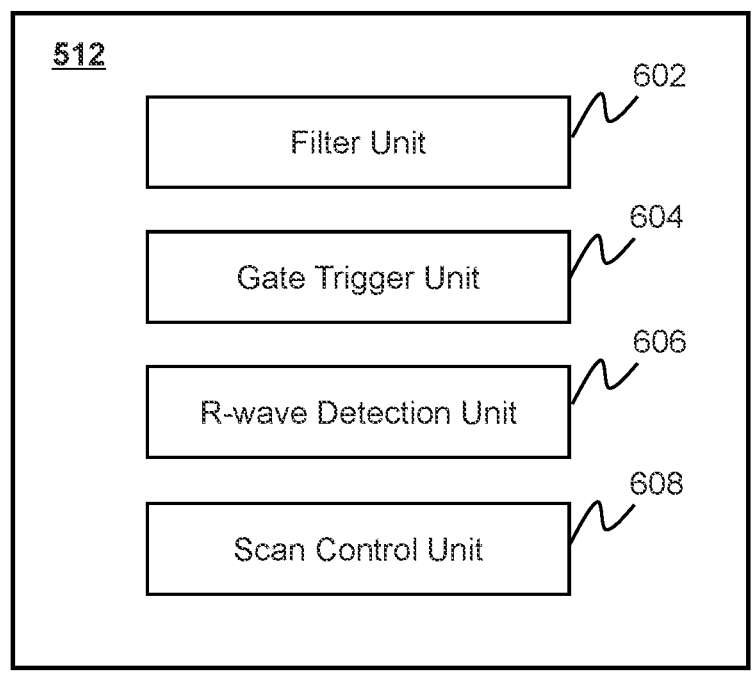
FIG. 6 is a block diagram illustrating an exemplary R-wave detection module according to some embodiments of the present disclosure.

As illustrated in FIG. 6, the R-wave detection module 512 may further include a filter unit 602, a gate trigger unit 604, an R-wave detection unit 606, and a scan control unit 608. In some embodiments, the filter unit 602 may filter the original ECG signal. For example, the filter unit 602 may filter the original ECG signal based on a low pass filter, such as an infinite impulse response (IIR) low pass filter. In some embodiments, the gate trigger unit 604 may determine whether to trigger a search gate based on the filtered ECG signal. The search gate may provide an instruction for triggering detection of R-wave. In response to a determination of triggering the search gate, the R-wave detection unit 606 may detect the R-wave on the original ECG signal. More descriptions of detecting the R-wave may be found elsewhere in the present disclosure (e.g., FIGS. 10-12, and the descriptions thereof). In some embodiments, the scan control unit 608 may operate an imaging device (e.g., the imaging device 110) to perform scans of the subject based on the detected R-wave. For example, the scan control unit 608 may determine a starting time of each scan based on the detected R-wave. Upon occurrence of the R-wave, the scan control unit 608 may count a delay time. After the delay time, the scan control unit 608 may send an instruction to the CT device for operating the CT device to begin the scan.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of components of the processing device 140 may include a storage device. Additionally or alternatively, the components of the processing device 140 may share a common storage device.

Figure 7:
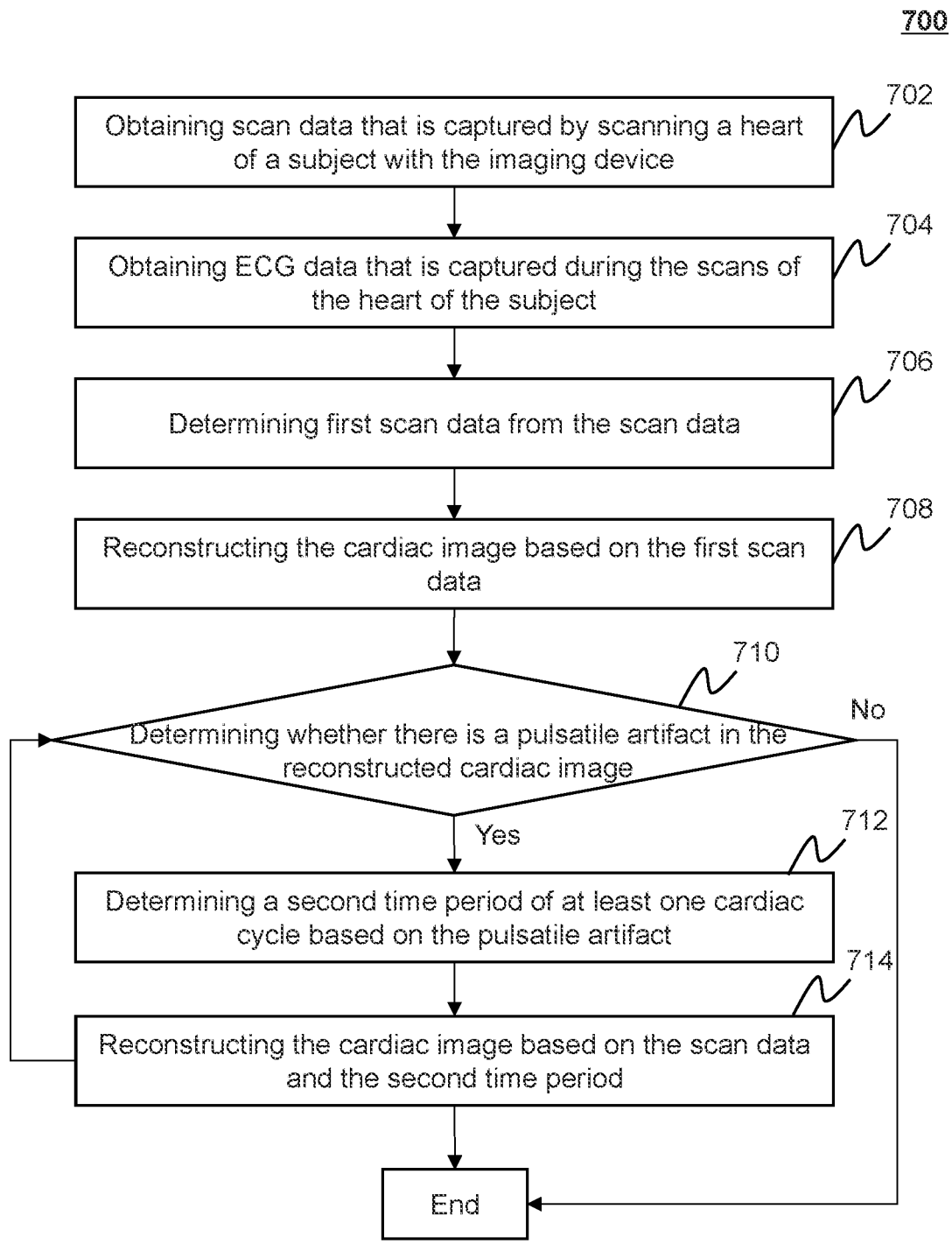
FIG. 7 is a flowchart illustrating an exemplary process for reconstructing a cardiac image according to some embodiments of the present disclosure.

FIG. 7 is a flowchart illustrating an exemplary process for reconstructing a cardiac image according to some embodiments of the present disclosure. In some embodiments, one or more operations of process 700 illustrated in FIG. 7 may be implemented in the imaging system 100 illustrated in FIG. 1. For example, the process 700 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In some embodiments, coronary computed tomography angiography (CCTA) may be a significant imaging technique for diagnosing cardiac or coronary artery disease by using a Multi-slice computed tomography (MSCT). Merely for illustration, in some embodiments, the process 700 may be implemented in connection with the CCTA.

In 702, the processor (e.g., the acquisition module 502 of the processing device 140) may obtain scan data that is captured by scanning a heart of a subject (e.g., a patient) with the imaging device (e.g., the imaging device 110).

The imaging device 110 may scan the heart of the subject to generate the scan data. In some embodiments, the scan data may be stored in a storage medium (e.g., the storage device 150, and/or the storage 220). The acquisition module 502 may obtain the scan data from the storage medium. In some embodiments, the acquisition module 502 may directly obtain the scan data in real time from the imaging device 110 during the scans.

In some embodiments, the imaging device 110 may include the CT scanner. The CT scanner may scan the heart of the subject, and generate corresponding scan data. For those skilled in the art, the heart of the subject always beats continuously during the scans. The heart beats may need to be considered in a process of reconstructing the cardiac image. In some embodiments, the ECG may be used to indicate and/or record the heart beats during the scans. The ECG data may indicate information related to the heart beats during the scans, for example, a cardiac cycle, a heart rate, an activation condition of atrium and/or ventricle, and so on.

In 704, the processor (e.g., the acquisition module 502 of the processing device 140) may obtain ECG data that is captured during the scans of the heart of the subject. The ECG data may include an ECG signal corresponding to a plurality of cardiac cycles. As used herein, each cardiac cycle may refer to a duration between two adjacent R-waves on the ECG. The cardiac cycle may be denoted as an R-R interval (i.e., an R-R for short).

In some embodiments, the processor may obtain the ECG data from a storage medium (e.g., the storage device 150, and/or the storage 220) of the imaging system 100. In some embodiments, the processor may obtain the ECG data from the imaging device 110 in real time or substantially real time during the scans. For example, the imaging device 110 may capture the ECG data in real time during the scans. As another example, a generic ECG acquisition collector, separated from the imaging device 110, may be configured to capture the ECG data, and send the captured ECG data to the imaging device 110 in real time, substantially real time, or periodically. The acquisition module 502 may obtain the ECG data from the imaging device 110. Exemplary ECG acquisition collector may include one or more sensors (e.g., electrons), one or more amplifying circuits, one or more filtering circuits, or the like, or any combination therefore. In some embodiments, the ECG acquisition collector may be integrated in the imaging device 110. During the scans, the imaging device 110 may generate the scan data and the ECG data synchronously. For example, the CCTA may apply a retrospectively electrocardiogram-gated spiral acquisition mode to scan the heart. During the scans by using the CCTA, the imaging device 110 may capture the scan data and the ECG data synchronously.

In 706, the processor (e.g., the reconstruction module 504 of the processing device 140) may determine first scan data from the scan data. The first scan data may include scan data corresponding to a first time period of each of the plurality of cardiac cycles.

The first time period refers to a certain phase of each of the plurality of cardiac cycles. The certain phase of each cardiac cycle is specified by using the imaging device 100. The first time period may be given as percentage of a duration of the cardiac cycle. In some embodiments, the duration of the cardiac cycle may be the time interval between two adjacent R-waves, that is, an R-R interval (i.e., an R-R for short). In some embodiments, the processor may predetermine the first time period by the imaging system 100. For example, the first time period may predetermined as 10% R-R, 20% R-R, 30% R-R, 40% R-R, 50% R-R, 60% R-R, 70% R-R, 80% R-R, and so on. In some embodiments, the first time period may be a default value predetermined by the imaging system 100. In some embodiments, the first time period may be adjusted according to different scenarios. For example, the first time period may be adjusted higher or lower when the imaging device 110 scans different subjects. As another example, the first time period may be adjusted to a second time period when the imaging system 100 detects that there is a pulsatile artifact in the reconstructed cardiac image. Note that the first time periods for a plurality of cardiac cycles may be in equal length or unequal length for each of the plurality of cardiac cycles. For example, assuming that the ECG includes three cardiac cycles, that is A, B, and C, the first time periods corresponding to A, B, and C respectively may be in equal length. As another example, the first time period corresponding to A may be in equal length to the first time period corresponding to B, however, in unequal length to the first time period corresponding to C. In some embodiments, the first time period may be configured as equal length for each cardiac cycle.

In some embodiments, for each cardiac cycle, the processor may determine a first reconstruction phase based on the first time period and an imaging window. The imaging window may indicate a width of the first reconstruction phase, for example, the width is equal to 10% R-R. In some embodiments, the first reconstruction phase may be a sum of the first time period and the imaging window. In other words, the first time period may be designated as the beginning of the first reconstruction phase, and the imaging window may be a width of the first reconstruction phase. For example, assuming that the first time period is 60% R-R, the width of the imaging window is 10% R-R, then the first reconstruction phase may include 60%-70% R-R. The beginning of the first reconstruction phase is 60% R-R, and the end of the reconstruction phase is 70% R-R. In some embodiments, the scan data corresponding to the first reconstruction phase may be used to reconstruct an image (e.g., a slice image). The processor may determine a plurality of first reconstruction phases for the plurality of cardiac cycles. Therefore, the processor may determine the first scan data that includes the scan data corresponding to the plurality of first reconstruction phases.

In 708, the processor (e.g., the reconstruction module 504 of the processing device 140) may reconstruct the cardiac image based on the first scan data. The reconstructed cardiac image may include a first image sequence or a three-dimensional (3D) image. The first image sequence may include one or more first images (e.g., slice images). The processor may reconstruct the 3D cardiac image based on the first image sequence.

In some embodiments, the processor may reconstruct each first image based on at least one part of the first scan data. For example, as the first scan data includes the scan data corresponding to the plurality of first reconstruction phases, each first image may be reconstructed based on part of the first scan data corresponding to the first reconstruction phase. Exemplary image reconstruction techniques may include filtered back projection (FBP), an algebraic reconstruction technology (ART), a statistical reconstruction (SR) algorithm, or the like, or any combination thereof. More descriptions of reconstructing the cardiac image may be found elsewhere in the present disclosure (e.g., FIG. 8, and the descriptions thereof).

In some embodiments, the processor may perform one or more iterations until the reconstructed cardiac image satisfies the requirement of qualified image. Specifically, the reconstructed cardiac image satisfies one or more image quality parameters. The one or more image quality parameters may include an image uniformity, a high contrast resolution, a low contrast resolution, a signal noise ratio (SNR), a CT number linearity, or the like, or any combination thereof. In some embodiments, the processor may perform the one or more iterations for reconstructing the cardiac image that is without the pulsatile substantially. For example, each iteration may include operations 710-714. As used herein, it is mention that the cardiac image is without the pulsatile artifact substantially, which means there is no completely or an almost negligible pulsatile artifact in the cardiac image. For example, if an area of pulsatile artifact is less than a value, the pulsatile artifact may be negligible.

For each iteration, the processor (e.g., the judgment module 506 of the processing device 140) may determine whether there is a pulsatile artifact in the reconstructed cardiac image, as illustrated in 710.

In some embodiments, the judgment module 506 may use a first machine-learned identification model to determine whether there is the pulsatile artifact in the reconstructed 3D cardiac image. For example, the reconstructed 3D cardiac image may be as input of the first machine-learned identification model. Accordingly, the first machine-learned identification model may output a value that indicates whether there is a pulsatile artifact in the reconstructed cardiac image. For example, if the output value is greater than or equal to a threshold, it is determined that there is the pulsatile artifact in the input cardiac image. If the output value is less than the threshold, it is determined that there is no pulsatile artifact in the input cardiac image.

Exemplary first machine-learned identification model may include an Extreme Gradient Boosting (Xgboost) model, a decision tree model, a Gradient Boosted Decision Tree (GBDT) model, a neural network model, or the like, or any combination thereof. It should be understood by those skilled in the art that the machine-learned identification model may be varied. All such variations are within the protection scope of the present disclosure.

In some embodiments, the judgment module 506 may determine whether there is a pulsatile artifact in the reconstructed cardiac image based on whether one or more vessels or tissues in the reconstructed cardiac image are continuous. If the one or more vessels or tissues in the reconstructed cardiac image are continuous, the judgment module 506 may determine that there is the pulsatile artifact in the reconstructed cardiac image. Otherwise, the judgment module 506 may determine that there is no pulsatile artifact substantially in the reconstructed cardiac image. In some embodiment, whether the one or more vessels or tissues in the reconstructed cardiac image are continuous may be determined by an experienced user (e.g., a doctor, a technician). The judgment module 506 may obtain the result judged by the experienced user, and further determine whether there is the pulsatile artifact in the reconstructed cardiac image. For example, if the experienced user judges that the one or more vessels or tissues in the reconstructed cardiac image are discontinuous, it is determined that there is the pulsatile artifact in the reconstructed cardiac image. In some embodiments, the judgment result may be represented by a character, a string, a binary value, etc. For example, the result, which indicates there is the pulsatile artifact in the reconstructed cardiac image, is represented by "0". The result, which indicates there is no pulsatile artifact substantially in the reconstructed cardiac image, is represented by "1".

In some embodiments, the judgment module 506 may determine whether there is a pulsatile artifact in the reconstructed cardiac image based on one or more image quality parameters. The one or more image quality parameters may include an image uniformity, a high contrast resolution, a low contrast resolution, a signal noise ratio (SNR), a CT number linearity, or the like, or any combination thereof. For example, if at least one image quality parameter is less than a predetermined quality threshold, the judgment module 506 may determine that there is the pulsatile artifact in the reconstructed cardiac image. Otherwise, the judgment module 506 may determine that there is no pulsatile artifact substantially in the reconstructed cardiac image.

In some embodiments, in response to the determination that there is no pulsatile artifact substantially in the reconstructed cardiac image, the processor may terminate the current iteration. The reconstructed cardiac image that is without the pulsatile artifact may be provided for medical diagnosis. In some embodiments, in response to the determination that there is the pulsatile artifact in the reconstructed cardiac image, the processor may proceed to operation 712.

In 712, the processor (e.g., the repair module 508 of the processing device 140) may determine a second time period of at least one cardiac cycle based on the pulsatile artifact. The second time period may be similar to the first time period, that is, a certain phase of each cardiac cycle (e.g., 80% R-R). The second time period may be given as percentage of a duration of the cardiac cycle.

In some embodiments, the processor may determine at least one first image with the pulsatile artifact from the first image sequence. The first image sequence may be generated based on the first scan data. The first image sequence may include one or more first images. Each of the one or more first images may be generated based on corresponding sub-first scan data. Each sub-first scan data may correspond to a cardiac cycle. The processor may determine the at least one cardiac cycle corresponding to the at least one first image having the pulsatile artifact based on capture time of the sub-first scan data. The processor may determine the second time period for the determined at least one cardiac cycle.

The processor may adjust the first time period corresponding to the at least one cardiac cycle to the second time period. The second time period may be different than the first time period. In some embodiments, a difference between the second time period and the first time period may be very small. In other words, the second time period may be obtained by adjusting the first time period slightly, which aims at avoiding generating new pulsatile artifact during reconstructing the cardiac image. For example, assuming that, for each of the at least one cardiac cycle, the first time period is 75% R-R. The processor may adjust the first time period (i.e., 75% R-R) to the second time period (e.g., 80% R-R, or 70% R-R). More descriptions of determining the second time period may be found elsewhere in the present disclosure (e.g., FIGS. 8-9, FIG. 13, and the descriptions thereof).

In 714, the processor (e.g., the repair module 508 of the processing device 150) may reconstruct the cardiac image based on the scan data and the second time period.

In some embodiments, the processor may determine third scan data based on the scan data, the at least one cardiac cycle corresponding to the at least one first image with the pulsatile artifact, and the second time period. The third scan data may be at least portion of the scan data. The third scan data may include scan data corresponding to the second time period. The processor may reconstruct at least one second image based on the third scan data. The at least one second image may correspond to the at least one cardiac cycle corresponding to the at least one first image with the pulsatile artifact. The processor may determine a second image sequence based on the first image sequence and the at least one second image. At least one second image of the second image sequence may replace the at least one first image with the pulsatile artifact. The second image sequence may include the first image sequence excluding the at least one first image with the pulsatile artifact, and the at least one second image. In some embodiments, the processor may reconstruct the cardiac image based on the second image sequence. More descriptions of reconstruct the cardiac image based on the scan data and the second time period may be found elsewhere in the present disclosure (e.g., FIG. 8, FIG. 13, and the descriptions thereof).

In some embodiments, the processor may determine whether there is the pulsatile artifact in the reconstructed image as illustrated in 710. If there is no pulsatile artifact substantially in the reconstructed cardiac image, the processor may terminate the current iteration. If there is the pulsatile artifact in the reconstructed cardiac image, the processor may perform a next iteration that includes the operations 710-714. The processor may complete the process 700 until there is no pulsatile artifact substantially in the reconstructed cardiac image. In other words, the processor may complete the process 700 until the reconstructed cardiac image satisfies the requirement of qualified image.

It should be noted that the description of the process 700 is provided for the purposes of illustration, and not intended to limit the scope of the present disclosure. For persons having ordinary skills in the art, various variations and modifications may be conducted under the teaching of the present disclosure. For example, the operations 712 and 714 may be integrated into a single operation. However, those variations and modifications may not depart from the protecting of the present disclosure.

Figure 8A:
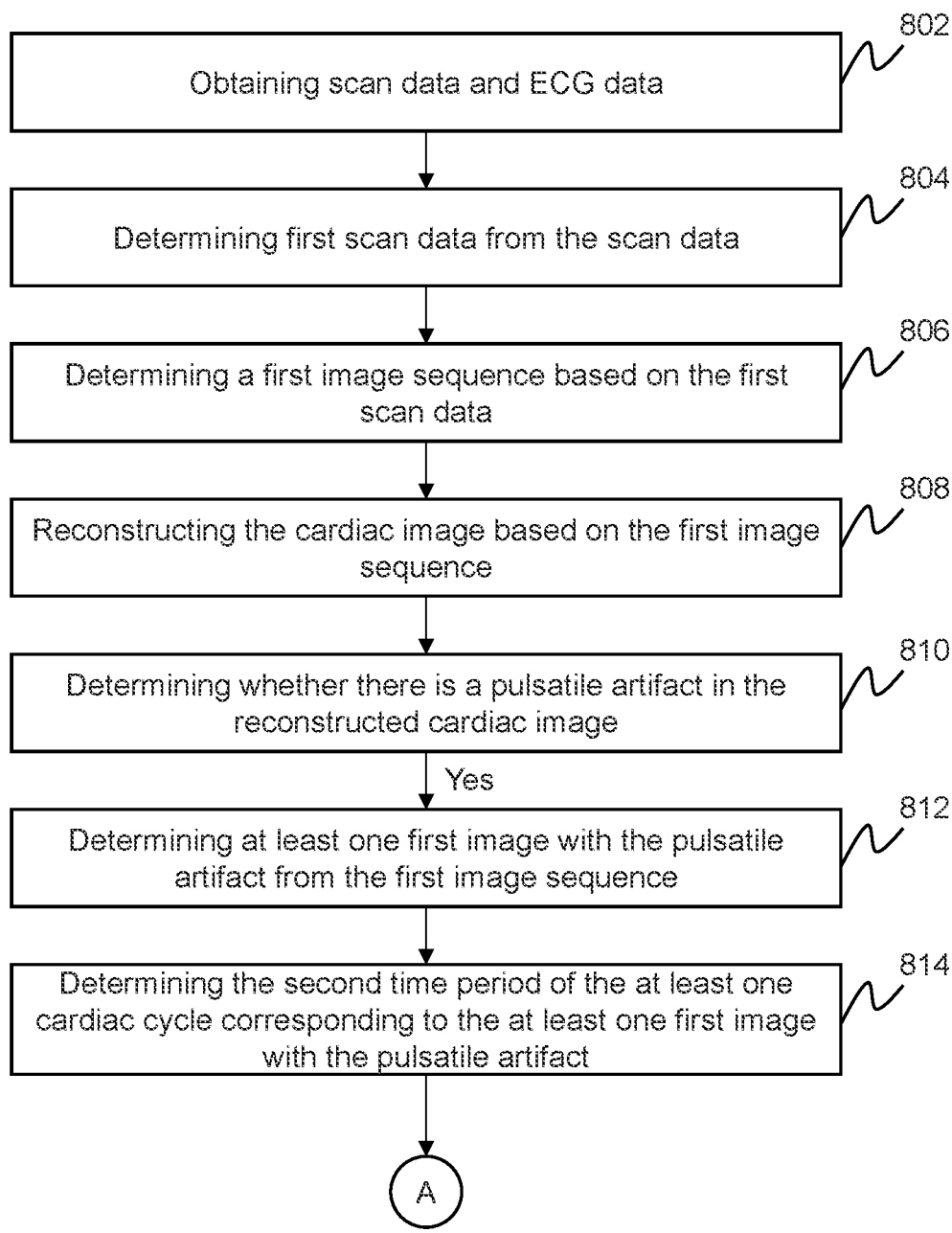
FIGS. 8A and 8B are flowcharts illustrating an exemplary process for reconstructing a medical image according to some embodiments of the present disclosure.
Figure 8B:
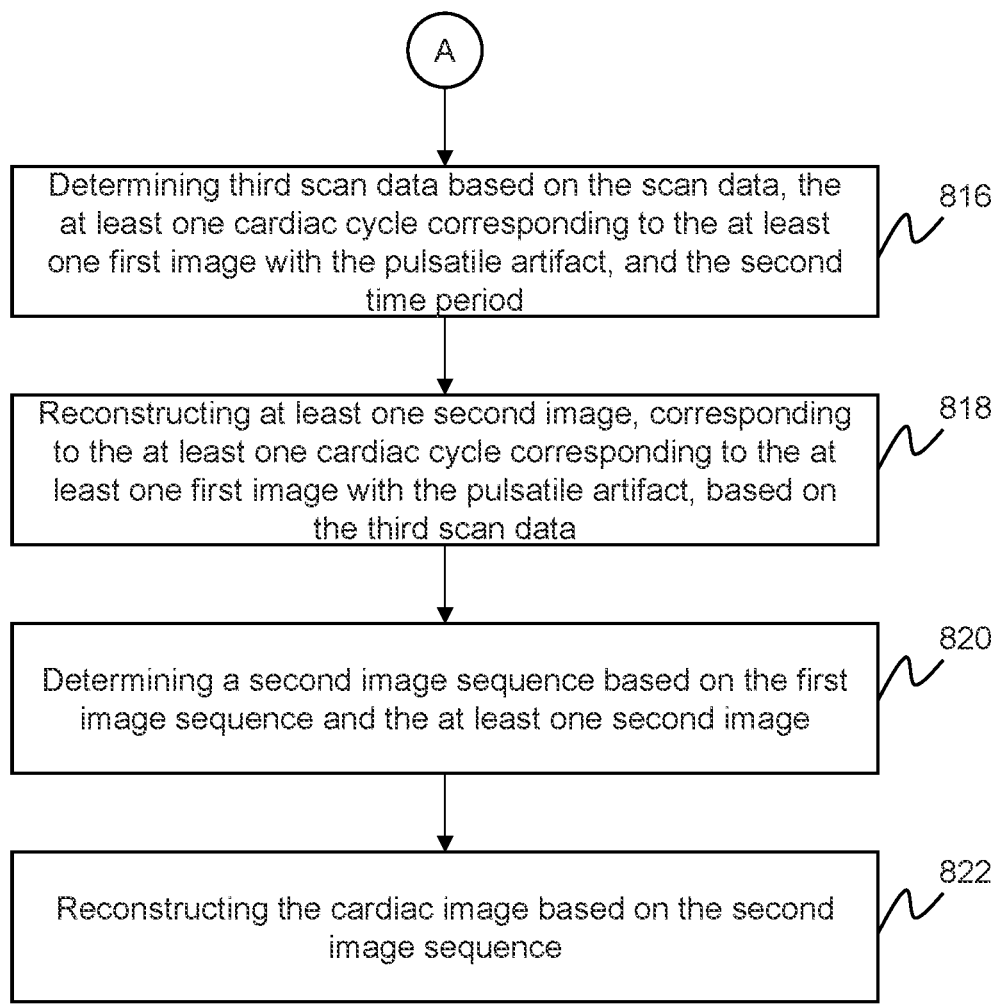

FIGS. 8A and 8B are flowcharts illustrating exemplary process for reconstructing a medical image according to some embodiments of the present disclosure. In some embodiments, one or more operations of the process 800 illustrated in FIG. 8 may be implemented in the imaging system 100 illustrated in FIG. 1. For example, the process 800 illustrated in FIG. 8 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, the processor (e.g., the acquisition module 502 of the processing device 140) may obtain scan data and ECG data. In some embodiments, the imaging device 110 may scan a heart of a subject to generate the scan data. In some embodiments, the scan data may be stored in a storage medium (e.g., the storage device 150, and/or the storage 220). The acquisition module 502 may obtain the scan data from the storage medium. In some embodiments, the acquisition module 502 may obtain the scan data in real time or substantially real time from the imaging device 110 during the scans.

During the scans, the scan data and the ECG data of the heart of the subject may be captured synchronously. The ECG data may indicate information related to heart beats during the scans, for example, a cardiac cycle, a heart rate, an activation condition of atrium and/or ventricle, and so on. In some embodiments, the ECG data may be stored in the storage medium (e.g., the storage device 150, and/or the storage 220) of the imaging device 110, the acquisition module 502 may obtain the ECG data from the storage medium.

In 804, the processor (e.g., the reconstruction module 504 of the processing device 140) may determine first scan data from the scan data. The first scan data may include scan data corresponding to a first time period of each of a plurality of cardiac cycles included in the ECG data.

The first time period refers to a certain phase of each of the plurality of cardiac cycles, e.g., 75% R-R. The certain phase of each cardiac cycle is specified by using the imaging device 100. The first time period may be given as percentage of a duration of the cardiac cycle. In some embodiments, the duration of the cardiac cycle may be the time interval between two adjacent R-waves, that is, an R-R interval (i.e., an R-R for short). In some embodiments, the processor may predetermine the first time period by the imaging system 100. For example, the first time period may predetermined as 10% R-R, 20% R-R, 30% R-R, 40% R-R, 50% R-R, 60% R-R, 70% R-R, 80% R-R, and so on. In some embodiments, the first time period may be a default value (e.g., 75% R-R). In some embodiments, the first time period may be adjusted according to different scenarios. For example, the first time period may be adjusted higher or lower when the imaging device 110 scans different subjects. As another example, the first time period may be adjusted to a second time period when the imaging system 100 detects that there is a pulsatile artifact in the reconstructed cardiac image. Note that the first time periods may be in equal length or unequal length for each of the plurality of cardiac cycles. In some embodiments, the first time period may be in equal length for each cardiac cycle.

In some embodiments, for each cardiac cycle, the processor may determine a first reconstruction phase based on the first time period and an imaging window. The imaging window may be a width of the first reconstruction phase, for example, the width is equal to 10% R-R. In some embodiments, the first reconstruction phase may be a sum of the first time period and the imaging window. In other words, the first time period may be designated as the beginning of the first reconstruction phase, and the imaging window may be a width of the reconstruction phase. For example, assuming that the first time period is 60% R-R, the width of the imaging window is 10% R-R, then the first reconstruction phase may include 60%-70% R-R. The beginning of the first reconstruction phase is 60% R-R, and the end of the reconstruction phase is 70% R-R. In some embodiments, the scan data corresponding to the first reconstruction phase may be used to reconstruct an image. The processor may determine a plurality of first reconstruction phases for the plurality of cardiac cycles. Therefore, the processor may determine the first scan data that includes the scan data corresponding to the plurality of first reconstruction phases.

In 806, the processor (e.g., the reconstruction module 504 of the processing device 140) may determine a first image sequence based on the first scan data. The first image sequence may include one or more first images. Each of the one or more first images may be a slice image. In some embodiments, the processor may reconstruct the one or more first images based on the first scan data. For example, for each cardiac cycle, a sub-first scan data may correspond to the first time period in the cardiac cycle. More particularly, the capture time of the sub-first scan data may be consistence with the time corresponding to the first reconstruction phase. The first reconstruction phase may be determined based on the first time period. The sub-first scan data may be a part of the first scan data. The reconstruction module 504 may reconstruct one first image based on the corresponding sub-first scan data. Similarly, the reconstruction module 504 may reconstruct the one or more first images based on the corresponding sub-first scan data.

Exemplary image reconstruction techniques may include filtered back projection (FBP), an algebraic reconstruction technology (ART), a statistical reconstruction (SR) algorithm, or the like, or any combination thereof. It should be understood by those skilled in the art that the image reconstruction technique may be varied. All such variations are within the protection scope of the present disclosure.

In 808, the processor (e.g., the reconstruction module 504 of the processing device 140) may reconstruct the cardiac image based on the first image sequence. In some embodiments, the cardiac image may include a three-dimensional (3D) image. For example, the reconstruction module 504 may utilize a three dimensional (3D) reconstruction method to generate the 3D cardiac image based on the first image sequence. Exemplary 3D reconstruction method may include a surface rendering method, a volume rendering method, or the like, or any combination thereof. Exemplary surface rendering method may include the shortest diagonal method, a Cuberille method, a Dividing Cubes method, a Marching Cubes (MC) method, or the like, or any combination thereof. Exemplary volume rendering method may include a ray casting method, a splatting method, a shear-warp method, a 3D texture-mapping hardware, or the like, or any combination thereof. In some embodiments, the reconstruction module 504 may access a commercial rendering tool (e.g., an OpenGL) by an application program interface (API) connected to the imaging system 100. The reconstruction module 504 may render the 3D cardiac image by using the commercial rendering tool.

In 810, the processor (e.g., the judgment module 506 of the processing device 140) may determine whether there is a pulsatile artifact in the reconstructed cardiac image.

In some embodiments, the judgment module 506 may use a first machine-learned identification model to determine whether there is the pulsatile artifact in the reconstructed 3D cardiac image. In some embodiments, the first machine-learned identification model may be stored in the storage medium (e.g., the storage device 150). The judgment module 506 may obtain the first machine-learned identification model from the storage medium. The reconstructed 3D cardiac image may be as input of the first machine-learned identification model. Accordingly, the first machine-learned identification model may output a value that indicates whether there is a pulsatile artifact in the reconstructed cardiac image. For example, if the output value is greater than or equal to a threshold, it is determined that there is the pulsatile artifact in the input cardiac image. If the output value is less than the threshold, it is determined that there is no pulsatile artifact in the input cardiac image.

Exemplary first machine-learned identification model may include an Extreme Gradient Boosting (Xgboost) model, a decision tree model, a Gradient Boosted Decision Tree (GBDT) model, a neural network model, or the like, or any combination thereof. The first machine-learned identification model may be trained based on a plurality of cardiac images. The plurality of cardiac images may include the cardiac images with the pulsatile artifact, and/or the cardiac images without the pulsatile artifact. A plurality of features associated with the plurality of cardiac images may be extracted. A plurality of parameters of the first machine-learned identification model may be determined by training the plurality of features. In some embodiments, the trained first machine-learned identification may be stored in the storage medium (e.g., the storage device 150, and or the storage 220). The judgment module 506 may invoke the first identification model from the storage medium, and determine whether there is the pulsatile artifact in the reconstructed cardiac image.

In some embodiments, the judgment module 506 may determine whether there is the pulsatile artifact in the reconstructed cardiac image based on a result indicating whether one or more vessels or tissues in the reconstructed cardiac image are continuous. If the one or more vessels or tissues in the reconstructed cardiac image are continuous, the judgment module 506 may determine that there is the pulsatile artifact in the reconstructed cardiac image. Otherwise, the judgment module 506 may determine that there is no pulsatile artifact substantially in the reconstructed cardiac image. In some embodiment, the result, indicating whether one or more vessels or tissues in the reconstructed cardiac image are continuous, may be determined by an experienced user (e.g., a doctor, a technician). The judgment module 506 may obtain the result judged by the experienced user, and further determine whether there is the pulsatile artifact in the reconstructed cardiac image. In some embodiments, the judgment result may be represented by a character, a string, a binary value, etc. For example, the result, which indicates there is the pulsatile artifact in the reconstructed cardiac image, is represented by "0". The result, which indicates there is no pulsatile artifact substantially in the reconstructed cardiac image, is represented by "1".

In some embodiments, the judgment module 506 may determine whether there is the pulsatile artifact in the reconstructed cardiac image based on one or more image quality parameters. The one or more image quality parameters may include an image uniformity, a high contrast resolution, a low contrast resolution, a signal noise ratio (SNR), a CT number linearity, or the like, or any combination thereof. For example, if at least one image quality parameter is less than a predetermined quality threshold, the judgment module 506 may determine that there is the pulsatile artifact in the reconstructed cardiac image.

In some embodiments, if there is the pulsatile artifact in the reconstructed cardiac image, in 812, the processor (e.g., the repair module 508 of the processing device 140) may determine at least one first image with the pulsatile artifact from the first image sequence.

In some embodiments, the processor may obtain coordinates (x,y,z) of the pulsatile artifact, and determine the at least one first image with the pulsatile artifact based on the coordinates. For example, assuming that the first image sequence includes five first images, A, B, C, D and E, and each first image may have its own coordinates. The repair module 508 may determine the at least one first image with the pulsatile artifact based on a relation of the coordinates of the pulsatile artifact and each slice image. For example, if the z-axis coordinate of the pulsatile artifact is consistence with the z-axis coordinate of image A, the image A may be the image with the pulsatile artifact. In some embodiments, the pulsatile artifact may be a region, the coordinates of the pulsatile artifact may include a plurality of coordinates of edges of the region.

In some embodiments, the repair module 508 may use the first machine-learned identification model to determine the at least one first image with the pulsatile artifact. The first machine-learned identification model may also be used to determine a position of the pulsatile artifact, for example, which images included in the first image sequence cause the pulsatile artifact of the 3D cardiac image.

In 814, the processor (e.g., the repair module 508 of the processing device 140) may determine the second time period of the at least one cardiac cycle corresponding to the at least one first image with the pulsatile artifact. The second time period may be similar to the first time period, that is, a certain phase of each cardiac cycle (e.g., 80% R-R). The certain phase of each cardiac cycle is specified by using the imaging device 100. The second time period may be given as percentage of a duration of the cardiac cycle.

Each of the at least one first image may be reconstructed based on corresponding sub-first scan data. Each sub-first scan data may correspond to a cardiac cycle. For example, the capture time of the sub-first scan data may fall in the corresponding cardiac cycle. The processor may determine the at least one cardiac cycle corresponding to the at least one first image with the pulsatile artifact based on the capture time of the sub-first scan data. The processor may determine the second time period for the determined at least one cardiac cycle. The processor may adjust the first time period corresponding to the at least one cardiac cycle to the second time period. The second time period may be different than the first time period. In some embodiments, a difference between the second time period and the first time period may be very small. In other words, the second time period may be determined by adjusting the first time period slightly. For example, assuming that, for each of the at least one cardiac cycle, the first time period is 75% R-R. The processor may adjust the first time period (i.e., 75% R-R) to the second time period (e.g., 80% R-R, or 70% R-R). Note that the adjusted second time period(s) may be in equal length or unequal length for the at least one cardiac cycle.

In 816, the processor (e.g., the repair module 508 of the processing device 140) may determine third scan data based on the scan data, the at least one cardiac cycle corresponding to the at least one first image with the pulsatile artifact, and the second time period.

In some embodiments, for each of the at least one cardiac cycle corresponding to the at least one first image with the pulsatile artifact, the processor may determine a second reconstruction phase based on the second time period and the imaging window (as illustrated in operation 804). The second reconstruction phase may be a sum of the second time period and the imaging window. For example, assuming that the second time period is determined as 75% R-R, the width of the imaging window is 10% R-R, the second reconstruction phase may include 75%-85% R-R. The processor may determine a sub-third scan data that includes scan data corresponding to the second reconstruction phase.

More particularly, the processor may determine the sub-third scan data that includes the scan data captured by the imaging device 110 during the duration of the second reconstruction phase. The processor may determine the third scan data that includes each sub-third scan data corresponding to the second reconstruction phase of each of the at least one cardiac cycle.

In 818, the processor (e.g., the repair module 508 of the processing device 140) may reconstruct at least one second image, corresponding to the at least one cardiac cycle corresponding to the at least one first image with the pulsatile artifact, based on the third scan data.

In some embodiments, for each of the at least one cardiac cycle corresponding to the at least one first image with the pulsatile artifact, the processor may reconstruct one second image based on corresponding sub-third scan data. In some embodiments, the number of the at least one second image may be equal to the number of the at least one first image. For example, assuming that there are three first images with the pulsatile artifact in the first image sequence, the processor may determine three second images that correspond to the cardiac cycles corresponding to the three first images.

In 820, the processor (e.g., the repair module 508 of the processing device 140) may determine a second image sequence based on the first image sequence and the at least one second image. For example, the at least one second image may replace the at least one first image with the pulsatile artifact. The second image sequence may include the first image sequence excluding the at least one first image with the pulsatile artifact, and the at least one second image.

In 830, the processor (e.g., the repair module 508 of the processing device 140) may reconstruct the cardiac image based on the second image sequence. The cardiac image may be a 3D cardiac image. Similar to operation 808, the repair module 508 may utilize the three dimensional (3D) reconstruction method to generate the 3D cardiac image based on the second image sequence.

It should be noted that the description of the process 800 is provided for the purposes of illustration, and not intended to limit the scope of the present disclosure. For persons having ordinary skills in the art, various variations and modifications may be conducted under the teaching of the present disclosure. However, those variations and modifications may not depart from the protecting of the present disclosure. For example, the processor may further determine whether there is the pulsatile artifact in the cardiac image reconstructed by the second image sequence. In response to a determination that there is the pulsatile artifact in the cardiac image, the processor may repeat at least one portion of the operations 810-812.

Figure 9:
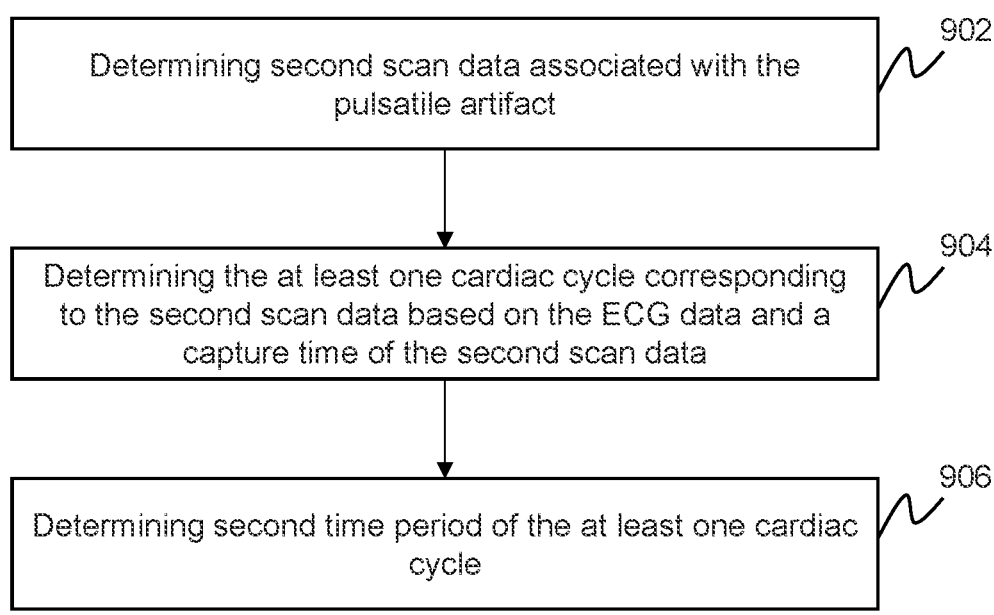
FIG. 9 is a flowchart illustrating an exemplary process for determining a second time period of at least one cardiac cycle according to some embodiments of the present disclosure.

FIG. 9 is a flowchart illustrating an exemplary process for determining a second time period of at least one cardiac cycle according to some embodiments of the present disclosure. In some embodiments, one or more operations of the process 900 illustrated in FIG. 9 may be implemented in the imaging system 100 illustrated in FIG. 1. For example, the process 900 illustrated in FIG. 9 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, the processor (e.g., the repair module 508 of the processing device 140) may determine second scan data associated with the pulsatile artifact.

In some embodiments, as illustrated in 812, the processor may determine at least one first image with the pulsatile artifact. Each of the at least one first image may be reconstructed based on corresponding sub-first scan data. As used herein, the sub-first scan data that is used to reconstruct the at least one first image may be designated as the second scan data. The second scan data may be at least one portion of the first scan data. In some embodiments, the second scan data may include each sub-first scan data related to each of the at least one first image with the pulsatile artifact.

In 904, the processor (e.g., the repair module 508 of the processing device 140) may determine the at least one cardiac cycle corresponding to the second scan data based on the ECG data and a capture time of the second scan data.

In some embodiments, the processor may obtain the capture time of the second scan data. Because the scan data and the ECG data may be captured synchronously during the scans, the processor may determine the at least one cardiac cycle corresponding to the capture time of the second scan data based on the ECG. For example, the second scan data may include a first sub-first scan data and a second sub-first scan data. The capture time of the first sub-first scan data and the second sub-first scan data may be T1 and T2 respectively. Based on the ECG, the repair module 508 may determine that the capture time T1 falls in the cardiac cycle A and the capture time T2 falls in the cardiac cycle B.

In 906, the processor (e.g., the repair module 508 of the processing device 140) may determine second time period of the at least one cardiac cycle. As illustrated in 814, the second time period may be similar to the first time period, that is, a certain phase of each cardiac cycle (e.g., 80% R-R). The second time period may be given as percentage of a duration of the cardiac cycle. More descriptions about determining the second time period may be found elsewhere in the present disclosure (e.g., FIGS. 7-8, and the descriptions thereof.

It should be noted that the above description of the process 900 is merely provided for the purposes of illustration, and not intended to limit the scope of the present disclosure. For persons having ordinary skills in the art, multiple variations and modifications may be made under the teachings of the present disclosure. For example, the operations 902 and 904 may be integrated in a single operation. However, those variations and modifications do not depart from the scope of the present disclosure.

Referring back to FIGS. 4A and 4B, the R-wave of the QRS complex may be the most significant wave among the components of one cycle of the ECG (i.e., the P-wave, the QRS complex, the T-wave). The R-wave may be defined as a beginning and/or an end of a cardiac cycle. During the medical imaging, the processor may need to detect the R-wave of each cardiac cycle based on the ECG data. In some embodiments, the processor may trigger the scan process based on the detected R-wave.

Figure 10:
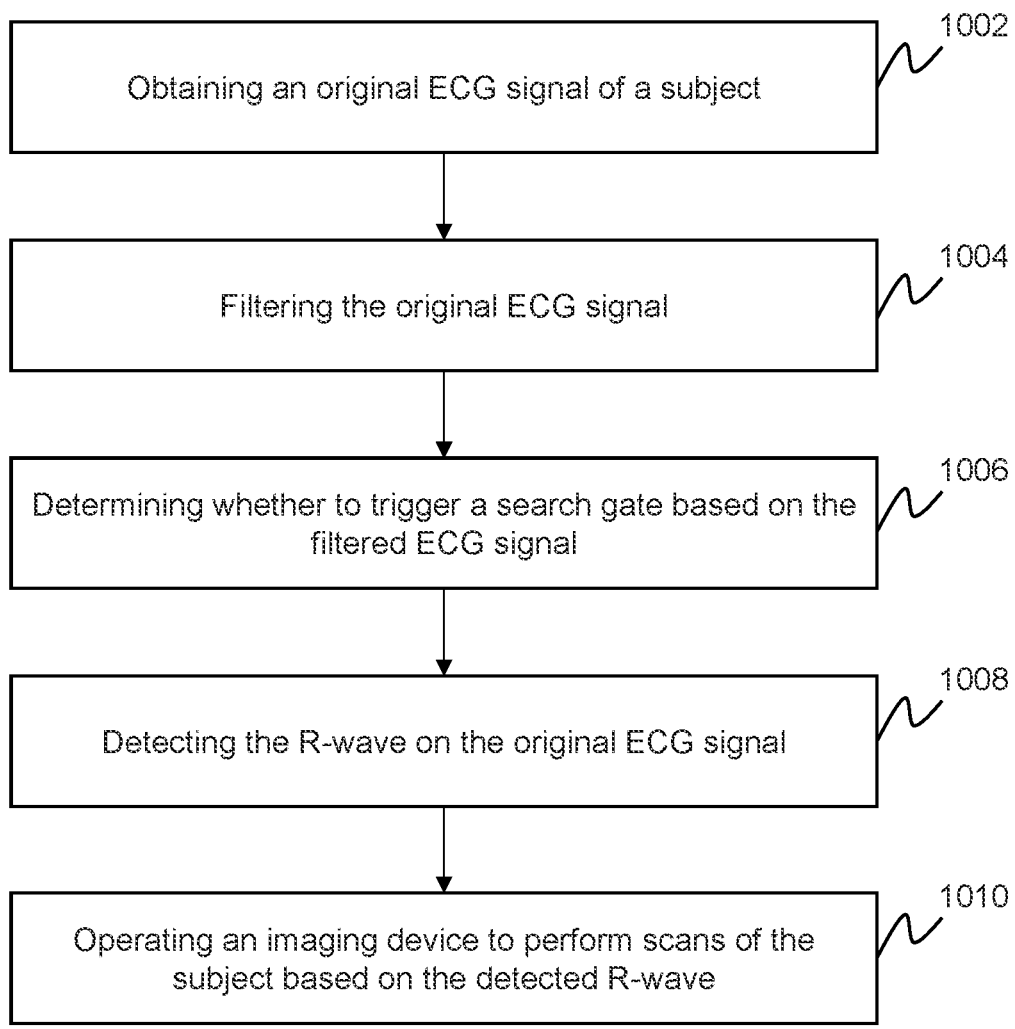
FIG. 10 is a flowchart illustrating an exemplary process for medical imaging according to some embodiments of the present disclosure.

FIG. 10 is a flowchart illustrating an exemplary process for medical imaging in one iteration according to some embodiments of the present disclosure. In some embodiments, one or more operations of the process 1000 illustrated in FIG. 10 may be implemented in the imaging system 100 illustrated in FIG. 1. For example, the process 1000 illustrated in FIG. 10 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1002, the processor (e.g., the R-wave detection module 512 of the processing device 140) may obtain an original ECG signal of a subject.

In some embodiments, the processor may obtain the original ECG signal from a storage medium (e.g., the storage device 150, and/or the storage 220) of the imaging system 100. For example, a generic ECG acquisition collector may be configured to obtain the original ECG signal, and store the obtained ECG signal in the storage device 150. The R-wave detection module 512 may obtain the original ECG signal from the storage device 150. In some embodiments, exemplary ECG acquisition collector may include one or more sensors (e.g., electrons), one or more amplifying circuits, one or more filtering circuits, or the like, or any combination therefore. In some embodiments, the ECG acquisition collector may be integrated to the imaging device 110 (e.g., the CT, the MRI, or the PET, etc.). The imaging device 110 may directly collect the original ECG signal of the subject during the scans. In some embodiments, the ECG acquisition collector may be separated from the imaging device 110. The original ECG signal captured by the ECG acquisition collector may be sent to the imaging device 110. The R-wave detection module 512 may obtain the original ECG signal from the imaging device 110.

In some embodiments, the obtained original ECG signal may be a digital ECG signal. The original ECG signal may include a plurality of samples. During the scans, the ECG acquisition collector may collect a sample in a pre-determined sampling rate in real time. The plurality of samples may form an ECG wave including one or more cycles, as illustrated in FIGS. 4A and 4B. There are one or more features associated with the original ECG signal, for example, a position, an amplitude, a peak width, a slope, etc. In some embodiments, the original ECG signal may be the ECG signal that is filtered and/or amplified by the ECG acquisition collector.

In 1004, the processor (e.g., the filter unit 602 of the R-wave detection module 512 of the processing device 140) may filter the original ECG signal.

In some embodiments, the processor may filter the original ECG signal based on a low pass filter. The low pass filter may filter out the signal whose frequency is greater than a threshold frequency (e.g., a cut-off frequency), and remain the signal whose frequency is no greater than a threshold frequency (e.g., a cut-off frequency). It should be understood that, the filtering for the original ECG signal aims at reducing or avoiding high-frequency noise of the original ECG signal.

In some embodiments, the low pass filter may be an infinite impulse response (IIR) low pass filter. For the IIR low pass filter, if an order of the filter (also referred to herein as filter order) is high, the computation may be more complex and the delay of the filtered ECG signal may be long. As used herein, the IIR filter having a low filter order may be utilized, which may reduce the delay of the filtered ECG signal. The filtering of the ECG signal may be processed in real time or substantially real time. In some embodiments, the filter order of the IIR low pass filter may include a first order, a second order, a third order, a fourth order, a fifth order, and so on. In some embodiments, the IIR low pass filter may include an ellipse filter. In some embodiments, the low pass filter may include a finite impulse response (FIR) filter.

In 1006, the processor (e.g., the gate trigger unit 604 of the R-wave detection module 512 of the processing device 140) may determine whether to trigger a search gate based on the filtered ECG signal. The search gate may provide an instruction for triggering detection of R-wave. For example, if one or more features of the filtered ECG signal are equal to or greater than a gate threshold, the search gate may be triggered to detect the R-wave. During the open of the search gate, the processor may detect the R-wave of the original ECG signal. In some embodiments, the one or more features may include but not limited to, a position of the P-wave, the QRS complex and/or the T-wave on the ECG, an amplitude of the P-wave, the QRS complex and/or the T-wave on the ECG, a peak width of the P-wave, the QRS complex and/or the T-wave on the ECG, a slope of the P-wave, the QRS complex and/or the T-wave on the ECG.

In some embodiments, the processor may determine a differential signal based on the filtered ECG signal. For example, the gate trigger unit 604 may use a first-order difference method to process the filtered ECG signal, and determine the differential signal. In some embodiments, if the differential signal is equal to or greater than the gate threshold, the processor may determine to trigger the search gate. Otherwise, the processor may determine not to trigger the search gate. Noted that, for those skilled in the art, when a signal is compared or calculated with other values in the disclosure, which means that an amplitude of the signal is used to compare or calculate with the other values.

In some embodiments, the processor may determine an amplified signal based on the differential signal. For example, the gate trigger unit 604 may use a nonlinear operation to process the differential signal, and determine the amplified signal. The nonlinear operation may be used to amplify the one or more features related to the high-frequency QRS complex. In some embodiments, the nonlinear operation may include an exponent arithmetic. In some embodiments, if the amplified signal is equal to or greater than the gate threshold, the processor may determine to trigger the search gate. Otherwise, the processor may determine not to trigger the search gate.

In some embodiments, the gate threshold may be a default value predetermined by the imaging system 100. In some embodiments, the gate threshold may be a dynamic value. For example, the gate trigger unit 604 may determine the dynamic gate threshold based on values of N samples of the filtered ECG signal. The N samples may include a current sample and N−1 previous samples. N is an integer and equal to or greater than 1.

In 1008, the processor (e.g., the R-wave detection unit 606 of the R-wave detection module 512 of the processing device 140) may detect the R-wave on the original ECG signal in response to a determination of triggering the search gate.

For example, in response to the determination of triggering the search gate, for each of a plurality of samples of the original ECG signal, the R-wave detection unit 606 may determine an amplitude difference between the sample and a signal baseline. The R-wave detection unit 606 may determine whether the amplitude difference is greater than an amplitude threshold. If the amplitude difference is greater than the amplitude threshold and the sample is above the signal baseline, the R-wave detection unit 606 may determine that the R-wave is an upward peak. The R-wave detection unit 606 may determine the first upward peak on the original ECG signal as the R-wave. If the amplitude difference is greater than the amplitude threshold and the sample is below the signal baseline, the R-wave detection unit 606 may determine that the R-wave is a downward peak. The R-wave detection unit 606 may determine the first downward peak on the original ECG signal as the R-wave.

In some embodiments, the processor may use a second machine-learned identification model to identify the R-wave. For example, the original ECG signal may be input to the second machine-learned identification model. The second machine-learned identification model may identify the R-wave and determine a position of the R-wave. More descriptions of the detecting the R-wave may be found elsewhere in the present disclosure (e.g., FIGS. 11-12, and the description thereof).

For those skilled in the art, each cardiac cycle may include a refractory period. According to the refractory period theory of an electrophysiological study, when a first R-wave appears, a second R-wave may not appear in the refractory period (e.g., 200 ms). In some embodiments, the processor may skip the refractory period to detect the second R-wave, which may reduce a false positive rate of the R-wave detection. In this case, during the refractory period, the processor may stop the operation of detecting R-wave and/or the operation of determining whether to trigger the search gate.

In 1010, the processor (e.g., the scan control unit 608 of the R-wave detection module 512 of the processing device 140) may operate an imaging device (e.g., the imaging device 110) to perform scans of the subject based on the detected R-wave.

For example, when CT scans the subject, the scan control unit 608 may need to consider the R-wave for determining a starting time of each scan. Upon occurrence of the R-wave, the scan control unit 608 may count a delay time. After the delay time, the scan control unit 608 may send an instruction to the CT device for operating the CT device to begin the scan. The processor may obtain the scan data from the CT device, and reconstruct a medical image based on the scan data. Exemplary reconstruction technique may include but not limit to a filter back projection (FBP), a convolution back projection (CBP), a direct Fourier transform algorithm, an algebraic reconstruction technique (ART). For those skilled in the art, the reconstruction technique may be various, any suitable reconstruction technique may be used to reconstruct the image.

In some embodiments, the delay time may be determined based on an R-R interval. The delay time may include a certain time (e.g., a certain phase of the R-R interval). The certain phase of the R-R interval is specified by using the imaging device system 100. For example, the certain phase of the R-R interval may be 10% R-R, 20% R-R, 30% R-R, 40% R-R, 50% R-R, 60% R-R, 70% R-R, 80% R-R, and so on. In some embodiments, the delay time may be a default value predetermined by the imaging system 100. In some embodiments, the delay time may be adjusted according to different scenarios. For example, during the scan, the heart rate of the subject may accelerate due to short breath holds, which shortens the R-R interval. If the delay time is not adjusted, the scan may cross a cardiac systolic period and a cardiac diastolic period, which causes the motion blur. The motion blur may degrade the quality of the reconstructed image. Therefore, the delay time may be adjusted dynamically for sake of improving the quality of the reconstructed image.

It should be noted that the above description is merely provided for the purposes of illustration, and not intended to limit the scope of the present disclosure. For persons having ordinary skills in the art, multiple variations and modifications may be made under the teachings of the present disclosure. For example, operation 1004 may be omitted. In 1006, the processor may determine whether to trigger a search gate based on the original ECG signal. However, those variations and modifications do not depart from the scope of the present disclosure.

Figure 11:
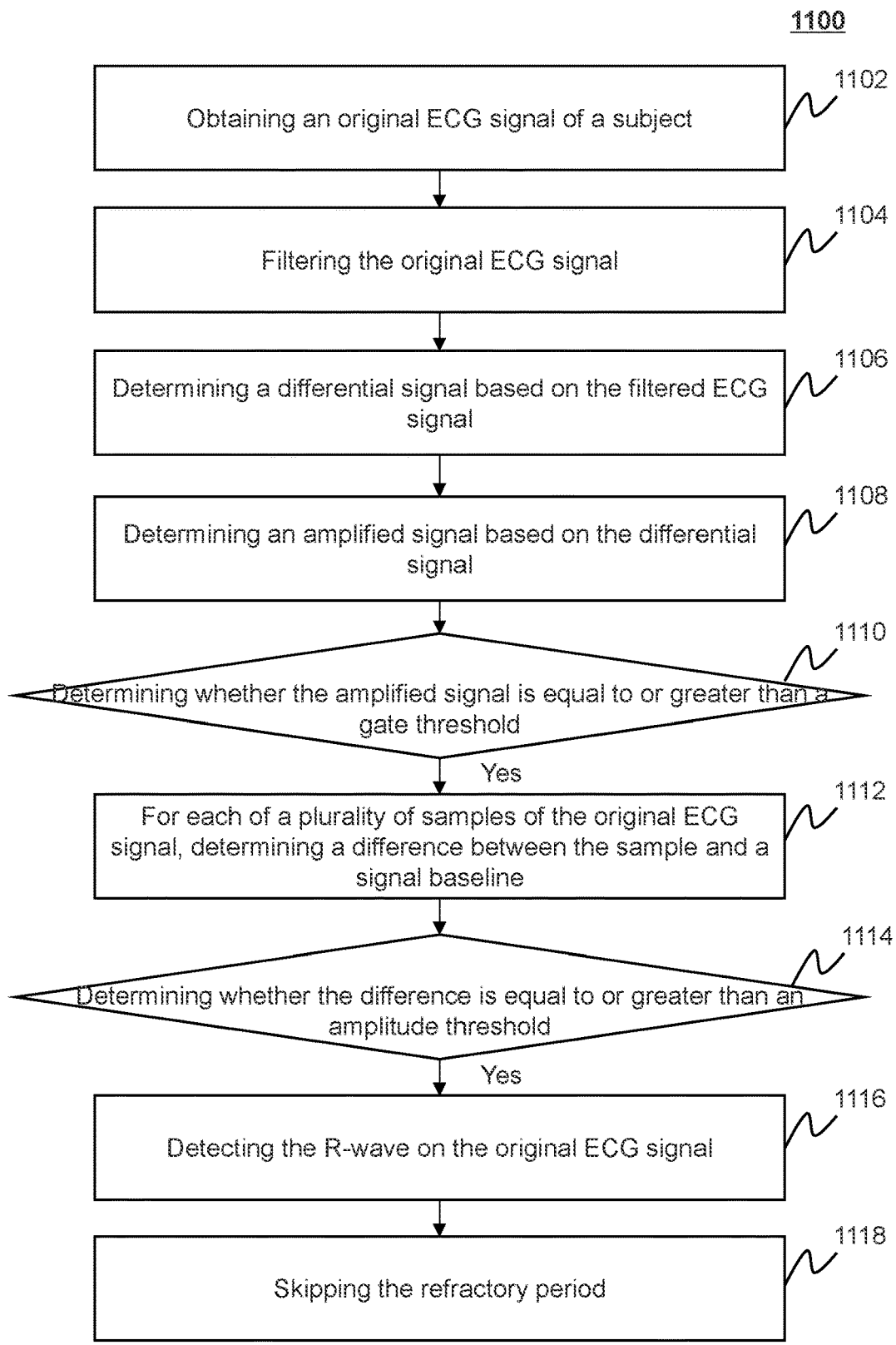
FIG. 11 is a flowchart illustrating an exemplary process for analyzing a R-wave according to some embodiments of the present disclosure.

FIG. 11 is a flowchart illustrating an exemplary process for analyzing an R-wave according to some embodiments of the present disclosure. In some embodiments, one or more operations of the process 1100 illustrated in FIG. 11 may be implemented in the imaging system 100 illustrated in FIG. 1. For example, the process 1100 illustrated in FIG. 11 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

Operations 1102-1104 may be similar to operations 1002-1004 of the process 1000 described above, the detailed descriptions of which may be found in this disclosure in connection with FIG. 10.

In some embodiments, the processor (e.g., the filter unit 602) may use a low pass filter to filter the original ECG signal. For example, the low pass filter may include an IIR filter. For those skilled in the art, the filter order of the low pass filter may cause the delay of the filtered ECG signal. In particular, if the filter order is high, the computation may be more complex and the delay of the filtered ECG signal may be long. Therefore, in some embodiments, by contrast with an FIR filter, the IIR low pass filter may use a low filter order to realize same or similar stop-band attenuation. In some embodiments, the filter order of the IIR low pass filter may include a first order, a second order, a third order, a fourth order, a fifth order, and so on. In some embodiments, the filter order may be determined according to parameters of the IIR low pass filter (e.g., a sample rate, a filtering pass-band, a stop-band, etc.). For example, assuming that the sample rate of the IIR low pass filter is 1000 Hz, the pass-band is 30-40 Hz, the stop-band attenuation is no less than 20 dB, the pass-band ripple is no greater than 0.05 dB, the IIR low pass filter may be designed as a fourth-order ellipse filter.

In 1106, the processor (e.g., the gate trigger unit 604) may a differential signal based on the filtered ECG signal. In some embodiments, the processor may use a first-order difference method to process the filtered ECG signal, and determine the differential signal. More particularly, the first-order difference method may be expressed according to Equation (1) as below:

$$y_d(n) = x(n) - x(n-1) \qquad (1),$$

wherein $x(n)$ denotes an n-th sample of the filtered ECG signal, $x(n-1)$ denotes an (n-1)-th sample of the filtered ECG signal, $y_d(n)$ denotes the differential signal.

In 1108, the processor (e.g., the gate trigger unit 604) may determine an amplified signal based on the differential signal. For example, the gate trigger unit 604 may use a nonlinear operation to process the differential signal, and determine the amplified signal. In some embodiments, the nonlinear operation may include an exponent arithmetic. The nonlinear operation may be expressed according to Equation (2) as below:

$$y_r(n) = y_d(n)^m \qquad (2),$$

wherein $y_r(n)$ denote the amplified signal. In some embodiments, the exponent m may be a non-negative numerical value, for m=4.

In 1110, the processor (e.g., the gate trigger unit 604) may determine whether the amplified signal is equal to or greater than a gate threshold.

If the amplified signal is equal to or greater than the gate threshold, the processor may proceed to operation 1112. Otherwise, the processor may return to the operation 1102 for continuing to obtain the original ECG signal in real time or substantially real time. In some embodiments, the gate threshold may be a default value predetermined by the imaging system 100. In some embodiments, the gate threshold may be a dynamic value.

For example, the dynamic gate threshold may be determined based on values of N samples of the filtered ECG signal. The N samples may include a current sample and N−1 previous samples, and N is an integer and equal to or greater than 1. In some embodiments, the dynamic gate threshold may be a product of an average value of amplified signals of the N samples and a first empirical factor. The dynamic gate threshold may be expressed according to Equation (3) as below:

$$f_{threshold}(n) = F_a \times \frac{1}{N} \sum_{k=1}^{N} y_r(k), \qquad (3)$$

where $f_{threshold}$ denotes the dynamic gate threshold, $F_a$ denotes the first empirical factor, $y_r(k)$ denotes the amplified signal of k-th sample, $k \in \{1, 2, \ldots, N\}$. In some embodiments, the first empirical factor $F_a$ may be equal to 0.5.

In some embodiments, the operation 1108 may be omitted. In the occasion, the processor may determine whether the differential signal is equal to or greater than the gate threshold. If the differential signal is equal to or greater than the gate threshold, the processor may trigger the search gate.

In 1112, in response to the determination of triggering the search gate, for each of a plurality of samples of the original ECG signal, the processor (e.g., the R-wave detection unit 606) may determine a difference between the sample and a signal baseline. In some embodiments, the signal baseline may associate with values of M samples of the original ECG signal. For example, the signal baseline may be an average value of the M samples of the original ECG signal. The signal baseline may be expressed according to Equation (4) as below:

$$f_{baseline}(n) = \frac{1}{M} \sum_{k=0}^{M-1} x(n-k), \qquad (4)$$

where $f_{baseline}(n)$ denotes the signal baseline, $x(n-k)$ denotes (n−k)-th sample of the original ECG signal, $k \in \{0, 1, \ldots, M-1\}$. In some embodiments, M may be equal to N.

In 1114, the processor (e.g., the R-wave detection unit 606) may determine whether the difference is equal to or greater than an amplitude threshold. If the difference is equal to or greater than the amplitude threshold, the processor may proceed to operation 1116.

In some embodiments, the amplitude threshold may associate with the plurality of differences between the plurality of samples and the signal baseline. For example, the amplitude threshold may be a product of a maximum value, among the absolute values of the plurality of differences, and a second empirical factor. The amplitude threshold may be expressed according to Equation (5) as below:

$$f_{ampthreshold} = F_b \times \max_{0 \le k \le N-1} |x(n-k) - f_{baseline}(n)|, \qquad (5)$$

where $f_{ampthreshold}$ denotes the amplitude threshold, $F_b$ denotes the second empirical factor, $x(n-k)$ denotes (n−k)-th sample of the original ECG signal, $k \in \{0,1, \ldots, N-1\}$, and $f_{baseline}^{(n)}$ denotes the signal baseline. In the embodiments, the second empirical factor $F_b$ may be equal to 0.3.

In 1116, in response to a determination that the difference is equal to or greater than the amplitude threshold, the processor (e.g., the R-wave detection unit 606) may detect the R-wave on the original ECG signal.

In some embodiments, the processor may determine a position of the sample that has a maximum value among absolute values of a plurality of the differences, as the position of the R-wave. For example, if the difference is greater than the amplitude threshold and the sample is above the signal baseline, the R-wave detection unit 606 may determine that the R-wave is an upward peak. The R-wave detection unit 606 may determine the first upward peak or a falling edge of the original ECG signal as the R-wave. As another example, if the difference is greater than the amplitude threshold and the sample is below the signal baseline, the R-wave detection unit 606 may determine that the R-wave is a downward peak. The R-wave detection unit 606 may determine the first downward peak or a rising edge of the original ECG signal as the R-wave. It should be understood, for each cardiac cycle indicated by the original ECG signal, the absolute value of the difference between the sample corresponding to the rising edge or the falling edge and the signal baseline may be the maximum.

In 1118, the processor (e.g., the R-wave detection unit 606) may skip the refractory period. In some embodiments, each cardiac cycle may include the refractory period. According to the refractory period theory of an electrophysiological study, when a first R-wave appears, a second R-wave may not appear in the refractory period (e.g., 200 ms). In some embodiments, upon occurrence of the first R-wave, the processor may skip the refractory period to detect the second R-wave.

In some embodiments, the processor (e.g., the scan control unit 608) may send an instruction to the imaging device 110 for operating the imaging device 110 to perform scans of the subject based on the detected R-wave.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, during the open of the search gate, the processor may use the second machine-learned identification model to detect the R-wave on the original ECG signal. The second machine-learned identification model may include but not limited to a conventional neural network (CNN), a Recurrent neural network (RNN), a deep neural network (DNN), and so on. The second machine-learned identification model may be used to identify the R-wave and determine a position of the R-wave.

Figure 12:
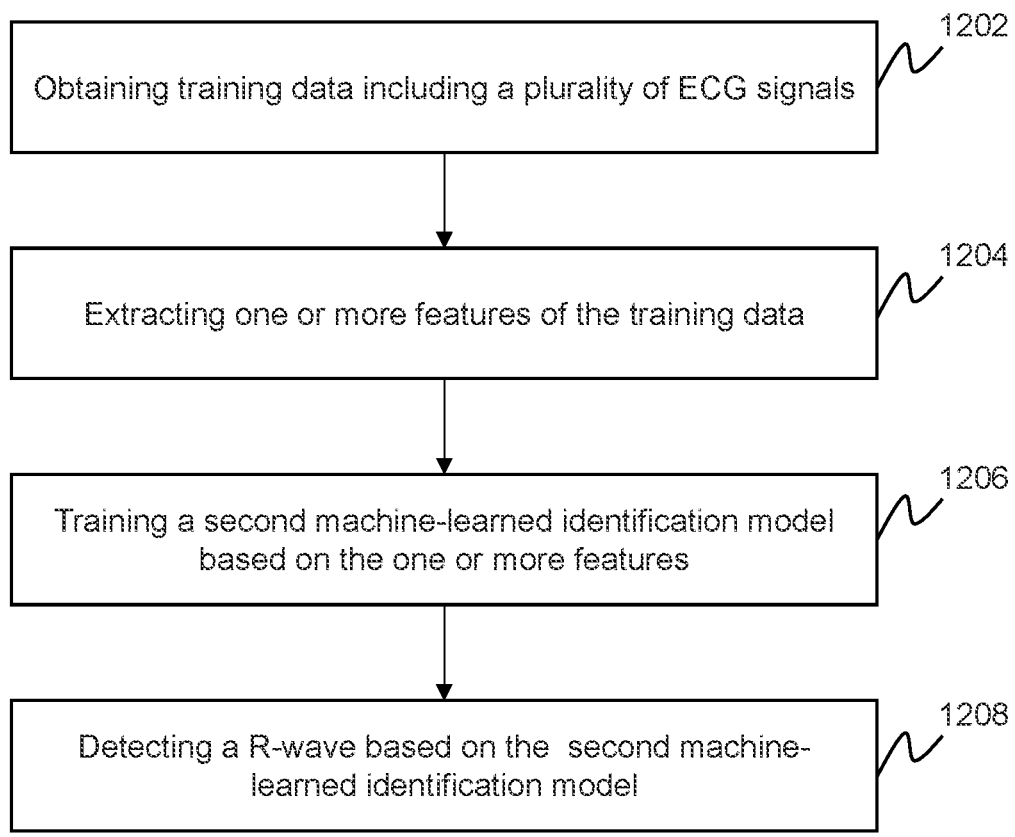
FIG. 12 is a flowchart illustrating an exemplary process for analyzing a R-wave according to some embodiments of the present disclosure.

FIG. 12 is a flowchart illustrating an exemplary process for analyzing an R-wave according to some embodiments of the present disclosure. In some embodiments, one or more operations of the process 1200 illustrated in FIG. 12 may be implemented in the imaging system 100 illustrated in FIG. 1. For example, the process 1200 illustrated in FIG. 12 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1202, the processor may obtain training data including a plurality of ECG signals. In some embodiments, the processor may obtain the plurality of ECG signals from a third-party database. For example, the third-party database may include a database of a medical organization that records a mass of ECG signals of the subjects. As another example, the third-party database may include an open source ECG database, such as a MIT-BIH database, an AHA database, a CES database. In some embodiments, the training data may include the plurality of original ECG signals. In some embodiments, the training data may include the plurality of ECG signals that are filtered and/or amplified.

In 1204, the processor may extract one or more features of the training data. The one or more features may include a position of the P-wave, the QRS complex and/or the T-wave on the ECG, an amplitude of the P-wave, the QRS complex and/or the T-wave on the ECG, a peak width of the P-wave, the QRS complex and/or the T-wave on the ECG, a slope of the P-wave, the QRS complex and/or the T-wave on the ECG, or the like, or any combination thereof.

In some embodiments, before extracting the one or more features of the training data, the processor may filter the training data (e.g., the plurality of ECG signals) for reducing noise jamming. The filter method may include a low pass filtering method, a band-pass filtering, a wavelet filtering, or the like, or any combination thereof.

In 1206, the processor may train a second machine-identification model based on the one or more features. Merely for illustration, the second machine-learned identification model is the DNN. The DNN may include a deep convolutional neural network (DCNN), a deep belief network (DBN), a random boolean network (RBN), or the like. The DNN may include a plurality of layers, for example, an input layer, one or more hidden layers and an output layer. For the plurality of layers, a latter layer may receive the output of a previous layer. The training data may be input to the input layer. The hidden layer may include a plurality of neural units for processing data. The output layer may output a prediction value. The processor may identify the R-wave based on the prediction value. For those skilled in the art, the second machine-learned identification model may be various, any suitable model may be applied to identify the R-wave, such variations may be within the scope of the present disclosure.

During the training, a plurality of parameters of the second machine-learned identification model may be determined by training the plurality of features. For example, the plurality of parameters may be trained based on a stochastic gradient descent (SGD). The parameters may include but not limited to weight matrixes, and/or bias terms. In some embodiments, the processor may train the plurality of parameters by minimizing a loss function of the second machine-learned model. When a loss value of the loss function is the minimum value or less than a loss threshold, the trained machine-learned identification may be designated as an optimal model for identifying the R-wave.

In 1208, the processor may detect an R-wave based on the second machine-learned identification model. In some embodiments, the trained second machine-learned identification model may be stored in a storage medium (e.g., the storage device 150). The processor may invoke the trained second machine-learned identification model to detect the R-wave. For example, the ECG signal may be as input of the second machine-learned identification model, and the second machine-learned identification model may identify the R-wave of the ECG signal, and output the corresponding position of the R-wave.

It should be noted that the above description is merely provided for the purposes of illustration, and not intended to limit the scope of the present disclosure. For persons having ordinary skills in the art, multiple variations and modifications may be made under the teachings of the present disclosure. For example, the second machine-learned identification model and the first machine-learned identification model illustrated in FIGS. 7-8 may be integrated into a single model. However, those variations and modifications do not depart from the scope of the present disclosure.

Figure 13:
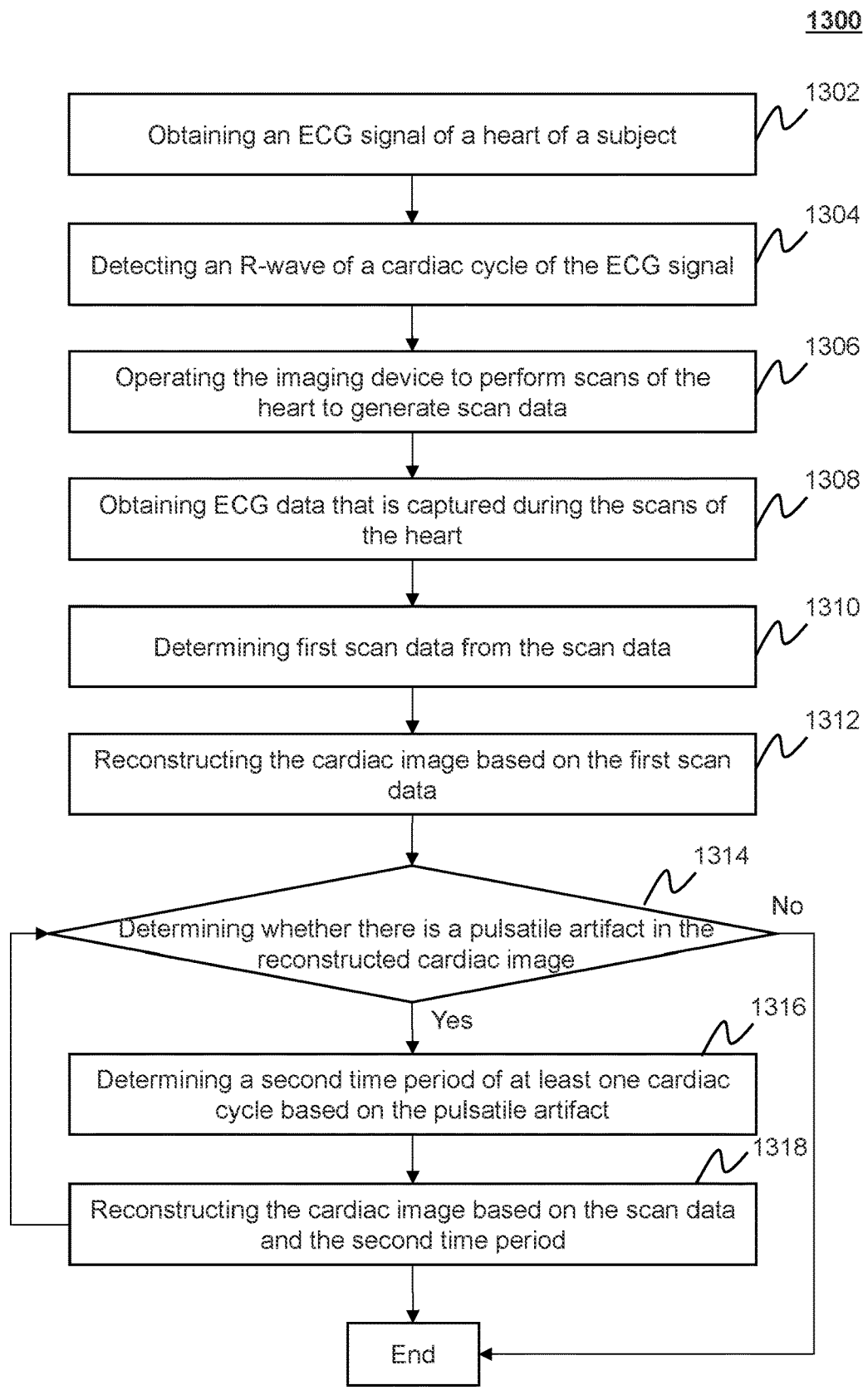
FIG. 13 is a flowchart illustrating an exemplary process for reconstructing a medical image according to some embodiments of the present disclosure.

FIG. 13 is a flowchart illustrating an exemplary process for reconstructing a medical image according to some embodiments of the present disclosure. In some embodiments, one or more operations of the process 1300 illustrated in FIG. 13 may be implemented in the imaging system 100 illustrated in FIG. 1. For example, the process 1300 illustrated in FIG. 13 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 5-6). The operations of the illustrated process presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1302, the processor (e.g., the R-wave detection module 512 of the processing device 140) may obtain an ECG signal of a heart of a subject.

In some embodiments, the processor may obtain the ECG signal from a storage medium (e.g., the storage device 150, and/or the storage 220) of the imaging system 100. For example, a generic ECG acquisition collector may be configured to obtain the ECG signal, and store the obtained ECG signal in the storage device 150. The R-wave detection module 512 may obtain the original ECG signal from the storage device 150. Exemplary ECG acquisition collector may include one or more sensors (e.g., electrons), one or more amplifying circuits, one or more filtering circuits, or the like, or any combination therefore. In some embodiments, the ECG acquisition collector may be integrated to the imaging device 110 (e.g., the CT, the MRI, or the PET, etc.). The imaging device 110 may directly collect the ECG signal of the subject in real time or substantially real time during the scans. In some embodiments, the ECG acquisition collector may be separated from the imaging device 110. The ECG signal captured by the ECG acquisition collector may be sent to the imaging device 110. The R-wave detection module 512 may obtain the ECG signal from the imaging device 110.

In 1304, the processor (e.g., the R-wave detection module 512 of the processing device 140) may detect an R-wave of a cardiac cycle of the ECG signal.

In some embodiments, the processor may filter the ECG signal based on a low pass filter. The processor may determine whether to trigger a search gate based on the filtered ECG signal. The search gate may provide an instruction for triggering detection of R-wave. Once the search gate is triggered, the processor may determine to detect the R-wave. For example, the R-wave detection module 512 may determine a differential signal based on the filtered ECG signal. If the differential signal is equal to or greater than a gate threshold, the processor may determine to trigger the search gate. Otherwise, the processor may determine not to trigger the search gate. As another example, the R-wave detection module 512 may determine an amplified signal based on the differential signal. In some embodiments, if the amplified signal is equal to or greater than the gate threshold, the processor may determine to trigger the search gate. Otherwise, the processor may determine not to trigger the search gate. More descriptions of the detection of the R-wave may be found elsewhere in the present disclosure (e.g., FIGS. 10-12, and the descriptions thereof), and not repeated herein.

In 1306, in response to the detection of the R-wave, the processor (e.g., the R-wave detection module 512 of the processing device 140) may operate the imaging device (e.g., the imaging device 110) to perform scans of the heart to generate scan data. In some embodiments, a starting time of each of the scans may be determined based on the R-wave of each cardiac cycle of the ECG signal.

For each scan, the scan starting time may be a time that is later than the time corresponding to the R-wave. Upon occurrence of the R-wave, the scan control unit 608 of the R-wave detection module 512 may hold to start the scan. For example, upon occurrence of the R-wave, the scan control unit 608 may hold a period of a delay time (e.g., 20 ms, 40 ms, 60 ms) before the scan. After the period of delay time, the scan control unit 608 may send an instruction to the imaging device 110 for operating the imaging device 110 device to begin the scan. During the scans, the imaging device 110 may generate the scan data.

In 1308, the processor (e.g., the acquisition module 502 of the processing device 140) may obtain ECG data that is captured during the scans of the heart. The ECG data may correspond to a plurality of cardiac cycles of the ECG signal. For example, the processor may obtain the ECG data from the R-wave detection module 512.

In 1310, the processor (e.g., the reconstruction module 504 of the processing device 140) may determine first scan data from the scan data. The first scan data may include scan data corresponding to a first time period of each of a plurality of cardiac cycles included in the ECG data. The first time period refers to a certain phase of each of the plurality of cardiac cycles. The certain phase of each cardiac cycle is specified by using the imaging device 100. The first time period may be given as percentage of a duration of the cardiac cycle. For example, the first time period may predetermined as 10% R-R, 20% R-R, 30% R-R, 40% R-R, 50% R-R, 60% R-R, 70% R-R, 80% R-R, and so on. In some embodiments, for each cardiac cycle, the processor may determine a first reconstruction phase based on the first time period and an imaging window. The processor may determine the first scan data that includes the scan data corresponding to a plurality of first reconstruction phases. Operation 1310 may be similar to operation 706 illustrated in FIG. 7 or operation 804 illustrated in FIG. 8A described above, the detailed descriptions of which may be found in this disclosure in connection with FIG. 7, FIG. 8A or FIG. 8B.

In 1312, the processor (e.g., the reconstruction module 504 of the processing device 140) may reconstruct the cardiac image based on the first scan data. For example, the reconstruction module 504 may reconstruct the cardiac image based on the first scan data by using a reconstruction method. Exemplary image reconstruction techniques may include filtered back projection (FBP), an algebraic reconstruction technology (ART), a statistical reconstruction (SR) algorithm, or the like, or any combination thereof. Operation 1312 may be similar to operation 708 illustrated in FIG. 7 or operation 808 illustrated in FIG. 8A described above, the detailed descriptions of which may be found in this disclosure in connection with FIG. 7, FIG. 8A or FIG. 8B.

In some embodiments, the processor may perform one or more iterations until the reconstructed cardiac image satisfies the requirement of qualified image. Specifically, the reconstructed cardiac image satisfies one or more image quality parameters. The one or more image quality parameters may include an image uniformity, a high contrast resolution, a low contrast resolution, a signal noise ratio (SNR), a CT number linearity, or the like, or any combination thereof. In some embodiments, the processor may perform the one or more iterations for reconstructing the cardiac image that is without the pulsatile substantially. Each iteration may include operations 1314-1318.

For each iteration, the processor (e.g., the judgment module 506 of the processing device 140) may determine whether there is a pulsatile artifact in the reconstructed cardiac image, as illustrated in 1314.

In some embodiments, the judgment module 506 may use a first machine-learned identification model to determine whether there is the pulsatile artifact in the reconstructed 3D cardiac image. The reconstructed 3D cardiac image may be input to the first machine-learned identification model. Accordingly, the first machine-learned identification model may output a value that indicates whether there is a pulsatile artifact in the reconstructed cardiac image. For example, if the output value is greater than or equal to a threshold, there is the pulsatile artifact in the input cardiac image. If the output value is less than the threshold, there is no pulsatile artifact in the input cardiac image.

In some embodiments, the judgment module 506 may determine whether there is the pulsatile artifact in the reconstructed cardiac image based on a result indicating whether one or more vessels or tissues in the reconstructed cardiac image are continuous. If the one or more vessels or tissues in the reconstructed cardiac image are continuous, the judgment module 506 may determine that there is the pulsatile artifact in the reconstructed cardiac image. Otherwise, the judgment module 506 may determine that there is no pulsatile artifact substantially in the reconstructed cardiac image. Operation 1314 may be similar to operation 710 illustrated in FIG. 7 or operation 810 illustrated in FIG. 8A described above, the detailed descriptions of which may be found in this disclosure in connection with FIG. 7, FIG. 8A or FIG. 8B.

In some embodiments, in response to the determination that there is no pulsatile artifact substantially in the reconstructed cardiac image, the processor may terminate the current iteration. The reconstructed cardiac image without the pulsatile artifact substantially may be provided for diagnosing the heart. In some embodiments, in response to the determination that there is the pulsatile artifact in the reconstructed cardiac image, the processor may proceed to operation 1316.

In 1316, the processor (e.g., the repair module 508 of the processing device 140) may determine a second time period of at least one cardiac cycle based on the pulsatile artifact. The second time period may be similar to the first time period, that is, a certain phase of each cardiac cycle (e.g., 80% R-R). The certain phase of each cardiac cycle is specified by using the imaging device 100. The second time period may also be given as percentage of a duration of the cardiac cycle.

In some embodiments, the processor (e.g., the repair module 508 of the processing device 140) may determine at least one first image with the pulsatile artifact from a first image sequence. The first image sequence may be generated based on the first scan data. The first image sequence may include one or more first images. Each of the one or more first images may be generated based on corresponding sub-first scan data. Each sub-first scan data may correspond to a cardiac cycle. Therefore, the processor may determine the at least one cardiac cycle corresponding to the at least one first image with the pulsatile artifact. Further, the processor may determine the second time period for the determined at least one cardiac cycle.

The processor may adjust the first time period corresponding to the at least one cardiac cycle to the second time period. The second time period may be different from the first time period. In some embodiments, a difference between the second time period and the first time period may be very small. In other words, the second time period may be determined by adjusting the first time period slightly. For example, assuming that, for each of the at least one cardiac cycle, the first time period is 75% R-R. The processor may adjust the first time period (i.e., 75% R-R) to the second time period (e.g., 80% R-R, or 70% R-R).

Operation 1316 may be similar to operation 712 illustrated in FIG. 7, operation 814 illustrated in FIG. 8A, or operations 902-906 illustrated in FIG. 9 described above, the detailed descriptions of which may be found in this disclosure in connection with FIG. 7, FIG. 8A, FIG. 8B or FIG. 9.

In 1318, the processor (e.g., the repair module 508 of the processing device 150) may reconstruct the cardiac image based on the scan data and the second time period.

In some embodiments, the processor may determine third scan data based on the scan data and the second time period. For each of the at least one cardiac cycle corresponding to the at least one first image with the pulsatile artifact, the processor may determine a second reconstruction phase based on the second time period and the imaging window. The processor may determine a sub-third scan data that includes scan data corresponding to the second reconstruction phase. More particularly, the processor may determine the sub-third scan data that includes the scan data captured by the imaging device 110 during the duration of the second reconstruction phase. The processor may determine the third scan data that includes each sub-third scan data corresponding to the second reconstruction phase of each of the at least one cardiac cycle.

In some embodiments, the processor may reconstruct at least one second image, corresponding to the at least one cardiac cycle corresponding to the at least one first image with the pulsatile artifact, based on the third scan data. For each of the at least one cardiac cycle, the processor may reconstruct one second image based on corresponding sub-third scan data. The processor may reconstruct a second sequence based on the first image sequence and the at least one second image. For example, the at least one second image may replace the at least one first image with the pulsatile artifact. The second image sequence may include the first image sequence excluding the at least one first image with the pulsatile artifact, and the at least one second image. In some embodiments, the processor may reconstruct the cardiac image based on the second image sequence. The cardiac image may be a 3D cardiac image.

It should be noted that the above description is merely provided for the purposes of illustration, and not intended to limit the scope of the present disclosure. For persons having ordinary skills in the art, multiple variations and modifications may be made under the teachings of the present disclosure. For example, operations 1306 and 1308 may be integrated into a single operation. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for analyzing an R-wave of an electrocardiogram (ECG) signal implemented on a computing device having one or more processors and one or more storage devices, the method comprising:
   obtaining an original ECG signal of a subject;
   filtering the original ECG signal;
   determining whether to trigger a search gate based on the filtered ECG signal, wherein the search gate is an instruction for detecting an R-wave on the original ECG signal; and
   detecting the R-wave on the original ECG signal in response to a determination of triggering the search gate, wherein
   the determining whether to trigger a search gate based on the filtered ECG signal includes:
      determining a differential signal based on the filtered ECG signal;
      determining an amplified signal based on the differential signal; and
      determining to trigger the search gate in response to that the amplified signal is equal to or greater than a gate threshold.

2. The method of claim 1, wherein the filtering the original ECG signal includes:
   filtering the original ECG signal based on an infinite impulse response (IIR) low pass filter.

3. The method of claim 1, wherein the gate threshold is determined based on values of N samples of the filtered ECG signal, wherein
   the N samples include a current sample and N−1 previous samples, and
   N is an integer and equal to or greater than 1.

4. The method of claim 1, wherein the detecting the R-wave on the original ECG signal in response to the determination of triggering the search gate includes:
   for each of a plurality of samples of the original ECG signal, determining a difference between the sample and a signal baseline;
   determining whether differences between the plurality of samples and the signal baseline are equal to or greater than an amplitude threshold; and
   in response to a determination that one or more of the differences are equal to or greater than the amplitude threshold, determining a position of the sample that has a maximum value among absolute values of the one or more of the differences, as a position of the R-wave.

5. The method of claim 4, wherein the amplitude threshold is associated with the differences between the plurality of samples and the signal baseline.

6. The method of claim 4, wherein the signal baseline is associated with values of M samples of the original ECG signal, wherein
   the M samples include a current sample and M−1 previous samples, and
   M is an integer and equal to or greater than 1.

7. The method of claim 1, wherein the method further includes:
   operating an imaging device to perform scans of the subject based on the detected R-wave, wherein a starting time of the scans is determined based an occurrence of the detected R-wave and a delay time.

8. The method of claim 7, wherein the delay time is determined based on an R-R interval.

9. The method of claim 1, wherein a machine-learned identification model is further configured to identify the R-wave and determine a position of the R-wave on the original ECG signal during an open of the search gate.

10. A system for analyzing an R-wave of an electrocardiogram (ECG) signal, comprising:
    at least one storage device including a set of instructions; and
    at least one processor in communication with the at least one storage device, wherein when executing the set of instructions, the at least one processor is directed to cause the system to:
    obtain an original ECG signal of a subject;
    filter the original ECG signal;
    determine whether to trigger a search gate based on the filtered ECG signal, wherein the search gate is an instruction for detecting an R-wave on the original ECG signal; and
    detect R-wave on the original ECG signal in response to a determination of triggering the search gate, wherein
    to determine whether to trigger a search gate based on the filtered ECG signal, the at least one processor is directed to cause the system to:
       determine a differential signal based on the filtered ECG signal;
       determine an amplified signal based on the differential signal; and
       determine to trigger the search gate in response to that the amplified signal is equal to or greater than a gate threshold.

11. The system of claim 10, wherein to filter the original ECG signal, the at least one processor is directed to cause the system to:
    filter the original ECG signal based on an infinite impulse response (IIR) low pass filter.

12. The system of claim 10, wherein the gate threshold is determined based on values of N samples of the filtered ECG signal, wherein
    the N samples include a current sample and N-1 previous samples, and
    N is an integer and equal to or greater than 1.

13. The system of claim 10, wherein to detect the R-wave on the original ECG signal in response to the determination of triggering the search gate, the at least one processor is directed to cause the system to:
    for each of a plurality of samples of the original ECG signal, determine a difference between the sample and a signal baseline;
    determine whether differences between the plurality of samples and the signal baseline are equal to or greater than an amplitude threshold; and
    in response to a determination that one or more of the differences are equal to or greater than the amplitude threshold, determine a position of the sample that has a maximum value among absolute values of the one or more of the differences, as a position of the R-wave.

14. The system of claim 13, wherein the amplitude threshold is associated with the differences between the plurality of samples and the signal baseline.

15. The system of claim 13, wherein the signal baseline is associated with values of M samples of the original ECG signal, wherein
    the M samples include a current sample and M−1 previous samples, and
    M is an integer and equal to or greater than 1.

16. The system of claim 10, wherein the at least one processor is directed to cause the system further to:
    operate an imaging device to perform scans of the subject based on the detected R-wave, wherein a starting time of the scans is determined based an occurrence of the detected R-wave and a delay time.

17. The system of claim 10, wherein a machine-learned identification model is further configured to identify the R-wave and determine a position of the R-wave on the original ECG signal during an open of the search gate.

18. A non-transitory computer readable medium, comprising at least one set of instructions for analyzing an R-wave of an electrocardiogram (ECG) signal, wherein when executed by one or more processors of a computing device, the at least one set of instructions causes the computing device to perform a method, the method comprising:
- obtaining an original ECG signal of a subject;
- filtering the original ECG signal;
- determining whether to trigger a search gate based on the filtered ECG signal, wherein the search gate is an instruction for detecting an R-wave on the original ECG signal; and
- detecting the R-wave on the original ECG signal in response to a determination of triggering the search gate, wherein
- the determining whether to trigger a search gate based on the filtered ECG signal includes:
  - determining a differential signal based on the filtered ECG signal;
  - determining an amplified signal based on the differential signal; and
  - determining to trigger the search gate in response to that the amplified signal is equal to or greater than a gate threshold.

* * * * *